US012484898B2

(12) United States Patent
Williams

(10) Patent No.: US 12,484,898 B2
(45) Date of Patent: Dec. 2, 2025

(54) SMALL DIAMETER LINEAR SURGICAL STAPLING APPARATUS

(71) Applicant: Covidien LP, Mansfield, MA (US)

(72) Inventor: Justin P. Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/413,627

(22) Filed: Jan. 16, 2024

(65) Prior Publication Data

US 2024/0148376 A1 May 9, 2024

Related U.S. Application Data

(63) Continuation of application No. 18/109,484, filed on Feb. 14, 2023, now Pat. No. 11,896,220, which is a continuation of application No. 17/407,623, filed on Aug. 20, 2021, now Pat. No. 11,576,671.

(51) Int. Cl.

| | |
|---|---|
| ***A61B 17/068*** | (2006.01) |
| ***A61B 17/00*** | (2006.01) |
| ***A61B 17/072*** | (2006.01) |

(52) U.S. Cl.

CPC ........ *A61B 17/0686* (2013.01); *A61B 17/072* (2013.01); *A61B 2017/00367* (2013.01); *A61B 2017/07257* (2013.01); *A61B 2017/07271* (2013.01); *A61B 2017/07285* (2013.01)

(58) Field of Classification Search

CPC .............. A61B 17/0686; A61B 17/072; A61B 2017/00367; A61B 2017/07257; A61B 2017/07285; A61B 2017/07271

See application file for complete search history.

(56) References Cited

U.S. PATENT DOCUMENTS

| | | | |
|---|---|---|---|
| 3,499,591 | A | 3/1970 | Green |
| 3,777,538 | A | 12/1973 | Weatherly et al. |
| 3,882,854 | A | 5/1975 | Hulka et al. |
| 4,027,510 | A | 6/1977 | Hiltebrandt |

(Continued)

FOREIGN PATENT DOCUMENTS

| | | | |
|---|---|---|---|
| AU | 198654765 | | 9/1986 |
| CA | 2773414 | A1 | 11/2012 |

(Continued)

OTHER PUBLICATIONS

International Search Report and Written Opinion for International Application No. PCT/IB2022/057649 dated Jan. 23, 2023.

(Continued)

*Primary Examiner* — Dariush Seif

(57) ABSTRACT

A surgical stapling apparatus includes a housing assembly and an adapter assembly defining a longitudinal axis and selectively attachable to the housing assembly. The adapter assembly supports an end effector including an anvil assembly, a cartridge assembly, and a spring lock. The cartridge assembly supports a plurality of fasteners and a sled that is movable through the cartridge assembly to fire the plurality of fasteners. The spring lock is supported on the sled. The spring lock is positioned to move from an unlocked position to a locked position when the sled moves through the cartridge assembly to prevent the cartridge assembly from being refired.

20 Claims, 18 Drawing Sheets

(56) References Cited

U.S. PATENT DOCUMENTS

| | | | |
|---|---|---|---|
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |
| 4,505,414 | A | 3/1985 | Filipi |
| 4,520,817 | A | 6/1985 | Green |
| 4,589,413 | A | 5/1986 | Malyshev et al. |
| 4,596,351 | A | 6/1986 | Fedotov et al. |
| 4,602,634 | A | 7/1986 | Barkley |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,861 | A | 1/1987 | Chow et al. |
| 4,633,874 | A | 1/1987 | Chow et al. |
| 4,671,445 | A | 6/1987 | Barker et al. |
| 4,700,703 | A | 10/1987 | Resnick et al. |
| 4,703,887 | A | 11/1987 | Clanton et al. |
| 4,728,020 | A | 3/1988 | Green et al. |
| 4,752,024 | A | 6/1988 | Green et al. |
| 4,784,137 | A | 11/1988 | Kulik et al. |
| 4,863,088 | A | 9/1989 | Redmond et al. |
| 4,869,415 | A | 9/1989 | Fox |
| 4,892,244 | A | 1/1990 | Fox et al. |
| 4,955,959 | A | 9/1990 | Tompkins et al. |
| 4,978,049 | A | 12/1990 | Green |
| 4,991,764 | A | 2/1991 | Mericle |
| 5,014,899 | A | 5/1991 | Presty et al. |
| 5,031,814 | A | 7/1991 | Tompkins et al. |
| 5,040,715 | A | 8/1991 | Green et al. |
| 5,065,929 | A | 11/1991 | Schulze et al. |
| 5,071,430 | A | 12/1991 | de Salis et al. |
| 5,074,454 | A | 12/1991 | Peters |
| 5,083,695 | A | 1/1992 | Foslien et al. |
| 5,084,057 | A | 1/1992 | Green et al. |
| 5,106,008 | A | 4/1992 | Tompkins et al. |
| 5,111,987 | A | 5/1992 | Moeinzadeh et al. |
| 5,129,570 | A | 7/1992 | Schulze et al. |
| 5,141,144 | A | 8/1992 | Foslien et al. |
| 5,156,315 | A | 10/1992 | Green et al. |
| 5,156,614 | A | 10/1992 | Green et al. |
| 5,163,943 | A | 11/1992 | Mohiuddin et al. |
| 5,170,925 | A | 12/1992 | Madden et al. |
| 5,171,247 | A | 12/1992 | Hughett et al. |
| 5,173,133 | A | 12/1992 | Morin et al. |
| 5,180,092 | A | 1/1993 | Crainich |
| 5,188,274 | A | 2/1993 | Moeinzadeh et al. |
| 5,220,928 | A | 6/1993 | Oddsen et al. |
| 5,221,036 | A | 6/1993 | Takase |
| 5,242,457 | A | 9/1993 | Akopov et al. |
| 5,246,156 | A | 9/1993 | Rothfuss et al. |
| 5,253,793 | A | 10/1993 | Green et al. |
| 5,263,629 | A | 11/1993 | Trumbull et al. |
| RE34,519 | E | 1/1994 | Fox et al. |
| 5,275,323 | A | 1/1994 | Schulze et al. |
| 5,282,807 | A | 2/1994 | Knoepfler |
| 5,289,963 | A | 3/1994 | McGarry et al. |
| 5,307,976 | A | 5/1994 | Olson et al. |
| 5,308,576 | A | 5/1994 | Green et al. |
| 5,312,023 | A | 5/1994 | Green et al. |
| 5,318,221 | A | 6/1994 | Green et al. |
| 5,326,013 | A | 7/1994 | Green et al. |
| 5,328,077 | A | 7/1994 | Lou |
| 5,330,486 | A | 7/1994 | Wilk |
| 5,332,142 | A | 7/1994 | Robinson et al. |
| 5,336,232 | A | 8/1994 | Green et al. |
| 5,344,061 | A | 9/1994 | Crainich |
| 5,352,238 | A | 10/1994 | Green et al. |
| 5,356,064 | A | 10/1994 | Green et al. |
| 5,358,506 | A | 10/1994 | Green et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,376,095 | A | 12/1994 | Ortiz |
| 5,379,933 | A | 1/1995 | Green et al. |
| 5,381,943 | A | 1/1995 | Allen et al. |
| 5,382,255 | A | 1/1995 | Castro et al. |
| 5,383,880 | A | 1/1995 | Hooven |
| 5,389,098 | A | 2/1995 | Tsuruta et al. |
| 5,395,033 | A | 3/1995 | Byrne et al. |
| 5,395,034 | A | 3/1995 | Allen et al. |
| 5,397,046 | A | 3/1995 | Savage et al. |
| 5,397,324 | A | 3/1995 | Carroll et al. |
| 5,403,312 | A | 4/1995 | Yates et al. |
| 5,405,072 | A | 4/1995 | Zlock et al. |
| 5,407,293 | A | 4/1995 | Crainich |
| 5,413,268 | A | 5/1995 | Green et al. |
| 5,415,334 | A | 5/1995 | Williamson et al. |
| 5,415,335 | A | 5/1995 | Knodell, Jr. |
| 5,417,361 | A | 5/1995 | Williamson, IV |
| 5,423,471 | A | 6/1995 | Mastri et al. |
| 5,425,745 | A | 6/1995 | Green et al. |
| 5,431,322 | A | 7/1995 | Green et al. |
| 5,431,323 | A | 7/1995 | Smith et al. |
| 5,433,721 | A | 7/1995 | Hooven et al. |
| 5,441,193 | A | 8/1995 | Gravener |
| 5,445,304 | A | 8/1995 | Plyley et al. |
| 5,447,265 | A | 9/1995 | Vidal et al. |
| 5,452,837 | A | 9/1995 | Williamson, IV et al. |
| 5,456,401 | A | 10/1995 | Green et al. |
| 5,464,300 | A | 11/1995 | Crainich |
| 5,465,895 | A | 11/1995 | Knodel et al. |
| 5,467,911 | A | 11/1995 | Tsuruta et al. |
| 5,470,007 | A | 11/1995 | Plyley et al. |
| 5,470,010 | A | 11/1995 | Rothfuss et al. |
| 5,472,132 | A | 12/1995 | Savage et al. |
| 5,474,566 | A | 12/1995 | Alesi et al. |
| 5,476,206 | A | 12/1995 | Green et al. |
| 5,478,003 | A | 12/1995 | Green et al. |
| 5,480,089 | A | 1/1996 | Blewett |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,486,185 | A | 1/1996 | Freitas et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,490,856 | A | 2/1996 | Person et al. |
| 5,497,933 | A | 3/1996 | DeFonzo et al. |
| 5,501,689 | A | 3/1996 | Green et al. |
| 5,505,363 | A | 4/1996 | Green et al. |
| 5,507,426 | A | 4/1996 | Young et al. |
| 5,518,163 | A | 5/1996 | Hooven |
| 5,518,164 | A | 5/1996 | Hooven |
| 5,529,235 | A | 6/1996 | Boiarski et al. |
| 5,531,744 | A | 7/1996 | Nardella et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,542,594 | A | 8/1996 | McKean et al. |
| 5,549,628 | A | 8/1996 | Cooper et al. |
| 5,551,622 | A | 9/1996 | Yoon |
| 5,553,765 | A | 9/1996 | Knodel et al. |
| 5,554,164 | A | 9/1996 | Wilson et al. |
| 5,554,169 | A | 9/1996 | Green et al. |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,701 | A | 10/1996 | Huitema et al. |
| 5,564,615 | A | 10/1996 | Bishop et al. |
| 5,571,116 | A | 11/1996 | Bolanos et al. |
| 5,573,169 | A | 11/1996 | Green et al. |
| 5,573,543 | A | 11/1996 | Akopov et al. |
| 5,575,799 | A | 11/1996 | Bolanos et al. |
| 5,575,803 | A | 11/1996 | Cooper et al. |
| 5,577,654 | A | 11/1996 | Bishop |
| 5,584,425 | A | 12/1996 | Savage et al. |
| 5,586,711 | A | 12/1996 | Plyley et al. |
| 5,588,580 | A | 12/1996 | Paul et al. |

(56) References Cited

U.S. PATENT DOCUMENTS

| | | | |
|---|---|---|---|
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A | 9/1997 | Bishop et al. | |
| 5,662,666 A | 9/1997 | Onuki et al. | |
| 5,665,085 A | 9/1997 | Nardella | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,690,269 A | 11/1997 | Bolanos et al. | |
| 5,690,675 A | 11/1997 | Sawyer et al. | |
| 5,692,668 A | 12/1997 | Schulze et al. | |
| 5,697,542 A | 12/1997 | Knodel et al. | |
| 5,702,409 A | 12/1997 | Rayburn et al. | |
| 5,704,534 A | 1/1998 | Huitema et al. | |
| 5,706,997 A | 1/1998 | Green et al. | |
| 5,709,334 A | 1/1998 | Sorrentino et al. | |
| 5,711,472 A | 1/1998 | Bryan | |
| 5,713,505 A | 2/1998 | Huitema | |
| 5,715,988 A | 2/1998 | Palmer | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,728,110 A | 3/1998 | Vidal et al. | |
| 5,732,806 A | 3/1998 | Foshee et al. | |
| 5,735,848 A | 4/1998 | Yates et al. | |
| 5,743,456 A | 4/1998 | Jones et al. | |
| 5,749,893 A | 5/1998 | Vidal et al. | |
| 5,752,644 A | 5/1998 | Bolanos et al. | |
| 5,762,255 A | 6/1998 | Chrisman et al. | |
| 5,762,256 A | 6/1998 | Mastri et al. | |
| 5,769,303 A | 6/1998 | Knodel et al. | |
| 5,769,892 A | 6/1998 | Kingwell | |
| 5,772,099 A | 6/1998 | Gravener | |
| 5,772,673 A | 6/1998 | Cuny et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,782,834 A | 7/1998 | Lucey et al. | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,810,811 A | 9/1998 | Yates et al. | |
| 5,810,855 A | 9/1998 | Rayburn et al. | |
| 5,814,055 A | 9/1998 | Knodel et al. | |
| 5,814,057 A | 9/1998 | Oi et al. | |
| 5,816,471 A | 10/1998 | Plyley et al. | |
| 5,817,109 A | 10/1998 | McGarry et al. | |
| 5,820,009 A | 10/1998 | Melling et al. | |
| 5,823,066 A | 10/1998 | Huitema et al. | |
| 5,826,776 A | 10/1998 | Schulze et al. | |
| 5,829,662 A | 11/1998 | Allen et al. | |
| 5,833,695 A | 11/1998 | Yoon | |
| 5,836,147 A | 11/1998 | Schnipke | |
| 5,862,972 A | 1/1999 | Green et al. | |
| 5,865,361 A | 2/1999 | Milliman et al. | |
| 5,871,135 A | 2/1999 | Williamson, IV et al. | |
| 5,873,873 A | 2/1999 | Smith et al. | |
| 5,878,938 A | 3/1999 | Bittner et al. | |
| 5,893,506 A | 4/1999 | Powell | |
| 5,894,979 A | 4/1999 | Powell | |
| 5,897,562 A | 4/1999 | Bolanos et al. | |
| 5,901,895 A | 5/1999 | Heaton et al. | |
| 5,911,352 A | 6/1999 | Racenet et al. | |
| 5,911,353 A | 6/1999 | Bolanos et al. | |
| 5,915,616 A | 6/1999 | Viola et al. | |
| 5,918,791 A | 7/1999 | Sorrentino et al. | |
| 5,919,198 A | 7/1999 | Graves, Jr. et al. | |
| 5,922,001 A | 7/1999 | Yoon | |
| 5,931,847 A | 8/1999 | Bittner et al. | |
| 5,941,442 A | 8/1999 | Geiste et al. | |
| 5,954,259 A * | 9/1999 | Viola | A61B 17/07207 227/176.1 |
| 5,964,394 A | 10/1999 | Robertson | |
| 5,964,774 A | 10/1999 | McKean et al. | |
| 5,980,510 A | 11/1999 | Tsonton et al. | |
| 5,988,479 A | 11/1999 | Palmer | |
| 6,004,335 A | 12/1999 | Vaitekunas et al. | |
| 6,010,054 A | 1/2000 | Johnson et al. | |
| 6,032,849 A | 3/2000 | Mastri et al. | |
| 6,045,560 A | 4/2000 | McKean et al. | |
| 6,063,097 A | 5/2000 | Oi et al. | |
| 6,079,606 A | 6/2000 | Milliman et al. | |
| 6,099,551 A | 8/2000 | Gabbay | |
| 6,109,500 A | 8/2000 | Alli et al. | |
| 6,131,789 A | 10/2000 | Schulze et al. | |
| 6,131,790 A | 10/2000 | Piraka | |
| 6,155,473 A | 12/2000 | Tompkins et al. | |
| 6,197,017 B1 | 3/2001 | Brock et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,279,809 B1 | 8/2001 | Nicolo | |
| 6,315,183 B1 | 11/2001 | Piraka | |
| 6,315,184 B1 | 11/2001 | Whitman | |
| 6,325,810 B1 | 12/2001 | Hamilton et al. | |
| 6,330,965 B1 | 12/2001 | Milliman et al. | |
| 6,391,038 B2 | 5/2002 | Vargas et al. | |
| 6,398,797 B2 | 6/2002 | Bombard et al. | |
| 6,436,097 B1 | 8/2002 | Nardella | |
| 6,439,446 B1 | 8/2002 | Perry et al. | |
| 6,443,973 B1 | 9/2002 | Whitman | |
| 6,478,804 B2 | 11/2002 | Vargas et al. | |
| 6,488,196 B1 | 12/2002 | Fenton, Jr. | |
| 6,503,257 B2 | 1/2003 | Grant et al. | |
| 6,505,768 B2 | 1/2003 | Whitman | |
| 6,544,274 B2 | 4/2003 | Danitz et al. | |
| 6,554,844 B2 | 4/2003 | Lee et al. | |
| 6,565,554 B1 | 5/2003 | Niemeyer | |
| 6,587,750 B2 | 7/2003 | Gerbi et al. | |
| 6,592,597 B2 | 7/2003 | Grant et al. | |
| 6,594,552 B1 | 7/2003 | Nowlin et al. | |
| 6,602,252 B2 | 8/2003 | Mollenauer | |
| 6,619,529 B2 | 9/2003 | Green et al. | |
| D480,808 S | 10/2003 | Wells et al. | |
| 6,644,532 B2 | 11/2003 | Green et al. | |
| 6,656,193 B2 | 12/2003 | Grant et al. | |
| 6,669,073 B2 | 12/2003 | Milliman et al. | |

(56) References Cited

U.S. PATENT DOCUMENTS 6,681,978 B2 1/2004 Geiste et al.
6,698,643 B2 3/2004 Whitman
6,716,232 B1 4/2004 Vidal et al.
6,722,552 B2 4/2004 Fenton, Jr.
6,755,338 B2 6/2004 Hahnen et al.
6,783,524 B2 8/2004 Anderson et al.
6,786,382 B1 9/2004 Hoffman
6,817,509 B2 11/2004 Geiste et al.
6,830,174 B2 12/2004 Hillstead et al.
6,835,199 B2 12/2004 McGuckin, Jr. et al.
6,843,403 B2 1/2005 Whitman
RE38,708 E 3/2005 Bolanos et al.
6,877,647 B2 4/2005 Green et al.
6,889,116 B2 5/2005 Jinno
6,905,057 B2 6/2005 Swayze et al.
6,945,444 B2 9/2005 Gresham et al.
6,953,138 B1 10/2005 Dworak et al.
6,953,139 B2 10/2005 Milliman et al.
6,959,852 B2 11/2005 Shelton, IV et al.
6,962,594 B1 11/2005 Thevenet
6,964,363 B2 11/2005 Wales et al.
6,978,921 B2 12/2005 Shelton, IV et al.
6,981,628 B2 1/2006 Wales
6,986,451 B1 1/2006 Mastri et al.
6,988,649 B2 1/2006 Shelton, IV et al.
6,991,627 B2 1/2006 Madhani et al.
6,994,714 B2 2/2006 Vargas et al.
7,000,818 B2 2/2006 Shelton, IV et al.
7,000,819 B2 2/2006 Swayze et al.
7,032,799 B2 4/2006 Viola et al.
7,044,352 B2 5/2006 Shelton, IV et al.
7,044,353 B2 5/2006 Mastri et al.
7,055,730 B2 6/2006 Ehrenfels et al.
7,055,731 B2 6/2006 Shelton, IV et al.
7,059,508 B2 6/2006 Shelton, IV et al.
7,070,083 B2 7/2006 Jankowski
7,083,075 B2 8/2006 Swayze et al.
7,097,089 B2 8/2006 Marczyk
7,111,769 B2 9/2006 Wales et al.
7,114,642 B2 10/2006 Whitman
7,121,446 B2 10/2006 Arad et al.
7,128,253 B2 10/2006 Mastri et al.
7,128,254 B2 10/2006 Shelton, IV et al.
7,140,527 B2 11/2006 Ehrenfels et al.
7,140,528 B2 11/2006 Shelton, IV
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,147,138 B2 12/2006 Shelton, IV
7,159,750 B2 1/2007 Racenet et al.
7,168,604 B2 1/2007 Milliman et al.
7,172,104 B2 2/2007 Scirica et al.
7,188,758 B2 3/2007 Viola et al.
7,207,471 B2 4/2007 Heinrich et al.
7,213,736 B2 5/2007 Wales et al.
7,225,963 B2 6/2007 Scirica
7,225,964 B2 6/2007 Mastri et al.
7,238,195 B2 7/2007 Viola
7,246,734 B2 7/2007 Shelton, IV
7,258,262 B2 8/2007 Mastri et al.
7,267,682 B1 9/2007 Bender et al.
7,278,562 B2 10/2007 Mastri et al.
7,278,563 B1 10/2007 Green
7,287,682 B1 10/2007 Ezzat et al.
7,293,685 B2 11/2007 Ehrenfels et al.
7,296,722 B2 11/2007 Ivanko
7,296,724 B2 11/2007 Green et al.
7,296,772 B2 11/2007 Wang
7,300,444 B1 11/2007 Nielsen et al.
7,303,107 B2 12/2007 Milliman et al.
7,303,108 B2 12/2007 Shelton, IV
7,308,998 B2 12/2007 Mastri et al.
7,326,232 B2 2/2008 Viola et al.
7,328,828 B2 2/2008 Ortiz et al.
7,328,829 B2 2/2008 Arad et al.
7,334,717 B2 2/2008 Rethy et al.
7,354,447 B2 4/2008 Shelton, IV et al.
7,357,287 B2 4/2008 Shelton, IV et al.
7,364,061 B2 4/2008 Swayze et al.
7,367,485 B2 5/2008 Shelton, IV et al.
7,377,928 B2 5/2008 Zubik et al.
7,380,695 B2 * 6/2008 Doll ................ A61B 17/07207
227/176.1
7,380,696 B2 6/2008 Shelton, IV et al.
7,396,356 B2 7/2008 Mollenauer
7,398,907 B2 7/2008 Racenet et al.
7,399,310 B2 7/2008 Edoga et al.
7,401,720 B1 7/2008 Durrani
7,401,721 B2 7/2008 Holsten et al.
7,404,508 B2 7/2008 Smith et al.
7,404,509 B2 7/2008 Ortiz et al.
7,407,074 B2 8/2008 Ortiz et al.
7,407,075 B2 8/2008 Holsten et al.
7,407,077 B2 8/2008 Ortiz et al.
7,407,078 B2 8/2008 Shelton, IV et al.
7,416,101 B2 8/2008 Shelton, IV et al.
7,419,080 B2 9/2008 Smith et al.
7,419,081 B2 9/2008 Ehrenfels et al.
7,419,495 B2 9/2008 Menn et al.
7,422,139 B2 9/2008 Shelton, IV et al.
7,424,965 B2 9/2008 Racenet et al.
7,431,189 B2 10/2008 Shelton, IV et al.
7,431,730 B2 10/2008 Viola
7,434,715 B2 10/2008 Shelton, IV et al.
7,434,717 B2 10/2008 Shelton, IV et al.
7,438,208 B2 10/2008 Larson
7,438,209 B1 10/2008 Hess et al.
7,441,684 B2 10/2008 Shelton, IV et al.
7,441,685 B1 10/2008 Boudreaux
7,448,525 B2 11/2008 Shelton, IV et al.
7,451,904 B2 11/2008 Shelton, IV
7,455,208 B2 11/2008 Wales et al.
7,455,676 B2 11/2008 Holsten et al.
7,458,494 B2 12/2008 Matsutani et al.
7,461,767 B2 12/2008 Viola et al.
7,462,185 B1 12/2008 Knodel
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,472,814 B2 1/2009 Mastri et al.
7,472,815 B2 1/2009 Shelton, IV et al.
7,472,816 B2 1/2009 Holsten et al.
7,473,258 B2 1/2009 Clauson et al.
7,481,347 B2 1/2009 Roy
7,481,348 B2 1/2009 Marczyk
7,481,349 B2 1/2009 Holsten et al.
7,481,824 B2 1/2009 Boudreaux et al.
7,487,899 B2 2/2009 Shelton, IV et al.
7,490,749 B2 2/2009 Schall et al.
7,494,039 B2 2/2009 Racenet et al.
7,500,979 B2 3/2009 Hueil et al.
7,503,474 B2 3/2009 Hillstead et al.
7,506,790 B2 3/2009 Shelton, IV
7,506,791 B2 3/2009 Omaits et al.
7,510,107 B2 3/2009 Timm et al.
7,513,408 B2 4/2009 Shelton, IV et al.
7,517,356 B2 4/2009 Heinrich
7,537,602 B2 5/2009 Whitman
7,543,729 B2 6/2009 Ivanko
7,543,730 B1 6/2009 Marczyk
7,543,731 B2 6/2009 Green et al.
7,552,854 B2 6/2009 Wixey et al.
7,556,185 B2 7/2009 Viola
7,556,186 B2 7/2009 Milliman
7,559,450 B2 7/2009 Wales et al.
7,559,452 B2 7/2009 Wales et al.
7,559,453 B2 7/2009 Heinrich et al.
7,559,937 B2 7/2009 de la Torre et al.
7,565,993 B2 7/2009 Milliman et al.
7,568,603 B2 8/2009 Shelton, IV et al.
7,568,604 B2 8/2009 Ehrenfels et al.

(56) References Cited

U.S. PATENT DOCUMENTS 7,571,845 B2 8/2009 Viola
7,575,144 B2 8/2009 Ortiz et al.
7,584,880 B2 9/2009 Racenet et al.
7,588,174 B2 9/2009 Holsten et al.
7,588,175 B2 9/2009 Timm et al.
7,588,176 B2 9/2009 Timm et al.
7,588,177 B2 9/2009 Racenet
7,597,229 B2 10/2009 Boudreaux et al.
7,597,230 B2 10/2009 Racenet et al.
7,600,663 B2 10/2009 Green
7,604,150 B2 10/2009 Boudreaux
7,604,151 B2 10/2009 Hess et al.
7,607,557 B2 10/2009 Shelton, IV et al.
7,611,038 B2 11/2009 Racenet et al.
7,617,961 B2 11/2009 Viola
7,624,902 B2 12/2009 Marczyk et al.
7,624,903 B2 12/2009 Green et al.
7,631,793 B2 12/2009 Rethy et al.
7,631,794 B2 12/2009 Rethy et al.
7,635,073 B2 12/2009 Heinrich
7,635,074 B2 12/2009 Olson et al.
7,635,373 B2 12/2009 Ortiz
7,637,409 B2 12/2009 Marczyk
7,637,410 B2 12/2009 Marczyk
7,641,091 B2 1/2010 Olson et al.
7,641,095 B2 1/2010 Viola
7,644,848 B2 1/2010 Swayze et al.
7,648,055 B2 1/2010 Marczyk
7,651,017 B2 1/2010 Ortiz et al.
7,654,431 B2 2/2010 Hueil et al.
7,658,311 B2 2/2010 Boudreaux
7,658,312 B2 2/2010 Vidal et al.
7,665,646 B2 2/2010 Prommersberger
7,665,647 B2 2/2010 Shelton, IV et al.
7,669,746 B2 3/2010 Shelton, IV
7,670,334 B2 3/2010 Hueil et al.
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,678,121 B1 3/2010 Knodel
7,681,772 B2 3/2010 Green et al.
7,682,367 B2 3/2010 Shah et al.
7,682,368 B1 3/2010 Bombard et al.
7,690,547 B2 4/2010 Racenet et al.
7,694,865 B2 4/2010 Scirica
7,699,205 B2 4/2010 Ivanko
7,703,653 B2 4/2010 Shah et al.
7,721,931 B2 5/2010 Shelton, IV et al.
7,721,933 B2 5/2010 Ehrenfels et al.
7,721,935 B2 5/2010 Racenet et al.
7,726,537 B2 6/2010 Olson et al.
7,726,538 B2 6/2010 Holsten et al.
7,726,539 B2 6/2010 Holsten et al.
7,731,072 B2 6/2010 Timm et al.
7,735,703 B2 6/2010 Morgan et al.
7,740,159 B2 6/2010 Shelton, IV et al.
7,740,160 B2 6/2010 Viola
7,743,960 B2 6/2010 Whitman et al.
7,744,628 B2 6/2010 Viola
7,753,245 B2 7/2010 Boudreaux et al.
7,753,248 B2 7/2010 Viola
7,757,924 B2 7/2010 Gerbi et al.
7,757,925 B2 7/2010 Viola et al.
7,762,445 B2 7/2010 Heinrich et al.
7,766,209 B2 8/2010 Baxter, III et al.
7,766,210 B2 8/2010 Shelton, IV et al.
7,766,924 B1 8/2010 Bombard et al.
7,766,928 B2 8/2010 Ezzat et al.
7,770,774 B2 8/2010 Mastri et al.
7,770,775 B2 8/2010 Shelton, IV et al.
7,776,060 B2 8/2010 Mooradian et al.
7,780,055 B2 8/2010 Scirica et al.
7,784,662 B2 8/2010 Wales et al.
7,789,283 B2 9/2010 Shah
7,789,889 B2 9/2010 Zubik et al.
7,793,812 B2 9/2010 Moore et al.
7,793,814 B2 9/2010 Racenet et al.
7,794,475 B2 9/2010 Hess et al.
7,798,385 B2 9/2010 Boyden et al.
7,798,386 B2 9/2010 Schall et al.
7,799,039 B2 9/2010 Shelton, IV et al.
7,810,690 B2 10/2010 Bilotti et al.
7,810,692 B2 10/2010 Hall et al.
7,810,693 B2 10/2010 Broehl et al.
7,815,090 B2 10/2010 Marczyk
7,815,091 B2 10/2010 Marczyk
7,815,092 B2 10/2010 Whitman et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,896 B2 10/2010 Racenet
7,823,760 B2 * 11/2010 Zemlok ............ A61B 17/07207
227/175.3
7,823,761 B2 11/2010 Boyden et al.
7,824,426 B2 11/2010 Racenet et al.
7,828,186 B2 11/2010 Wales
7,828,187 B2 11/2010 Green et al.
7,828,188 B2 11/2010 Jankowski
7,828,189 B2 11/2010 Holsten et al.
7,832,408 B2 11/2010 Shelton, IV et al.
7,832,611 B2 11/2010 Boyden et al.
7,832,612 B2 11/2010 Baxter, III et al.
7,834,630 B2 11/2010 Damadian et al.
7,837,079 B2 11/2010 Holsten et al.
7,837,081 B2 11/2010 Holsten et al.
7,841,503 B2 11/2010 Sonnenschein et al.
7,845,533 B2 12/2010 Marczyk et al.
7,845,534 B2 12/2010 Viola et al.
7,845,535 B2 12/2010 Scircia
7,845,537 B2 12/2010 Shelton, IV et al.
7,845,538 B2 12/2010 Whitman
7,850,703 B2 12/2010 Bombard et al.
7,857,183 B2 12/2010 Shelton, IV
7,857,184 B2 12/2010 Viola
7,857,185 B2 12/2010 Swayze et al.
7,857,186 B2 12/2010 Baxter, III et al.
7,861,906 B2 1/2011 Doll et al.
7,861,907 B2 1/2011 Green et al.
7,866,524 B2 1/2011 Krehel
7,866,525 B2 1/2011 Scirica
7,866,526 B2 1/2011 Green et al.
7,866,527 B2 1/2011 Hall et al.
7,866,528 B2 1/2011 Olson et al.
7,870,989 B2 1/2011 Viola et al.
7,886,952 B2 2/2011 Scirica et al.
7,891,532 B2 2/2011 Mastri et al.
7,891,533 B2 2/2011 Green et al.
7,891,534 B2 2/2011 Wenchell et al.
7,896,214 B2 3/2011 Farascioni
7,900,805 B2 3/2011 Shelton, IV et al.
7,901,416 B2 3/2011 Nolan et al.
7,905,380 B2 3/2011 Shelton, IV et al.
7,905,381 B2 3/2011 Baxter, III et al.
7,909,039 B2 3/2011 Hur
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,543 B2 3/2011 Roth et al.
7,918,230 B2 4/2011 Whitman et al.
7,922,061 B2 4/2011 Shelton, IV et al.
7,922,063 B2 4/2011 Zemlok et al.
7,922,064 B2 4/2011 Boyden et al.
7,926,691 B2 4/2011 Viola et al.
7,926,692 B2 4/2011 Racenet et al.
7,934,628 B2 5/2011 Wenchell et al.
7,934,630 B2 5/2011 Shelton, IV et al.
7,934,631 B2 5/2011 Balbierz et al.
7,942,300 B2 5/2011 Rethy et al.
7,942,303 B2 5/2011 Shah
7,950,560 B2 5/2011 Zemlok et al.

(56) References Cited

U.S. PATENT DOCUMENTS 7,950,561 B2 5/2011 Aranyi
7,950,562 B2 5/2011 Beardsley et al.
7,954,682 B2 6/2011 Giordano et al.
7,954,683 B1 6/2011 Knodel et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,959,051 B2 6/2011 Smith et al.
7,963,431 B2 6/2011 Scirica
7,963,432 B2 6/2011 Knodel et al.
7,963,433 B2 6/2011 Whitman et al.
7,967,178 B2 6/2011 Scirica et al.
7,967,179 B2 6/2011 Olson et al.
7,967,180 B2 6/2011 Scirica
7,975,894 B2 7/2011 Boyden et al.
7,980,443 B2 7/2011 Scheib et al.
7,988,026 B2 8/2011 Knodel et al.
7,988,027 B2 8/2011 Olson et al.
7,988,028 B2 8/2011 Farascioni et al.
7,992,758 B2 8/2011 Whitman et al.
7,997,468 B2 8/2011 Farascioni
7,997,469 B2 8/2011 Olson et al.
8,002,795 B2 8/2011 Beetel
8,006,885 B2 8/2011 Marczyk
8,006,887 B2 8/2011 Marczyk
8,007,505 B2 8/2011 Weller et al.
8,007,513 B2 8/2011 Nalagatla et al.
8,011,550 B2 9/2011 Aranyi et al.
8,011,551 B2 9/2011 Marczyk et al.
8,011,552 B2 9/2011 Ivanko
8,011,553 B2 9/2011 Mastri et al.
8,011,555 B2 9/2011 Tarinelli et al.
8,012,170 B2 9/2011 Whitman et al.
8,015,976 B2 9/2011 Shah
8,016,177 B2 9/2011 Bettuchi et al.
8,016,178 B2 9/2011 Olson et al.
8,020,742 B2 9/2011 Marczyk
8,020,743 B2 9/2011 Shelton, IV
8,028,882 B2 10/2011 Viola
8,028,883 B2 10/2011 Stopek
8,028,884 B2 10/2011 Sniffin et al.
8,033,438 B2 10/2011 Scirica
8,033,440 B2 10/2011 Wenchell et al.
8,033,441 B2 10/2011 Marczyk
8,033,442 B2 10/2011 Racenet et al.
8,034,077 B2 10/2011 Smith et al.
8,038,044 B2 10/2011 Viola
8,038,045 B2 10/2011 Bettuchi et al.
8,052,024 B2 11/2011 Viola et al.
8,056,787 B2 11/2011 Boudreaux et al.
8,056,788 B2 11/2011 Mastri et al.
8,056,791 B2 11/2011 Whitman
8,061,577 B2 11/2011 Racenet et al.
8,066,166 B2 11/2011 Demmy et al.
8,070,033 B2 12/2011 Milliman et al.
8,070,034 B1 12/2011 Knodel
8,070,035 B2 12/2011 Holsten et al.
8,074,858 B2 12/2011 Marczyk
8,074,859 B2 12/2011 Kostrzewski
8,074,862 B2 12/2011 Shah
8,083,118 B2 12/2011 Milliman et al.
8,083,119 B2 12/2011 Prommersberger
8,083,120 B2 12/2011 Shelton, IV et al.
8,087,563 B2 1/2012 Milliman et al.
8,091,753 B2 1/2012 Viola
8,091,754 B2 1/2012 Ehrenfels et al.
8,091,756 B2 1/2012 Viola
8,092,493 B2 1/2012 Marczyk
8,096,459 B2 1/2012 Ortiz et al.
8,096,460 B2 1/2012 Blier et al.
8,100,309 B2 1/2012 Marczyk
8,100,310 B2 1/2012 Zemlok
8,102,008 B2 1/2012 Wells
8,113,405 B2 2/2012 Milliman
8,113,406 B2 2/2012 Holsten et al.
8,113,407 B2 2/2012 Holsten et al.
8,113,408 B2 2/2012 Wenchell et al.
8,113,409 B2 2/2012 Cohen et al.
8,113,410 B2 2/2012 Hall et al.
8,123,101 B2 2/2012 Racenet et al.
8,127,975 B2 3/2012 Olson et al.
8,127,976 B2 3/2012 Scirica et al.
8,132,703 B2 3/2012 Milliman et al.
8,132,705 B2 3/2012 Viola et al.
8,132,706 B2 3/2012 Marczyk et al.
8,136,713 B2 3/2012 Hathaway et al.
8,141,762 B2 3/2012 Bedi et al.
8,152,041 B2 4/2012 Kostrzewski
8,157,148 B2 4/2012 Scirica
8,157,150 B2 4/2012 Viola et al.
8,157,151 B2 4/2012 Ingmanson et al.
8,157,152 B2 4/2012 Holsten et al.
8,162,197 B2 4/2012 Mastri et al.
8,167,185 B2 5/2012 Shelton, IV et al.
8,167,186 B2 5/2012 Racenet et al.
8,172,121 B2 5/2012 Krehel
8,172,124 B2 5/2012 Shelton, IV et al.
8,181,837 B2 5/2012 Roy
8,186,555 B2 5/2012 Shelton, IV et al.
8,186,557 B2 5/2012 Cohen et al.
8,186,558 B2 5/2012 Sapienza
8,186,559 B1 5/2012 Whitman
8,186,560 B2 5/2012 Hess et al.
8,193,044 B2 6/2012 Kenneth
8,196,795 B2 6/2012 Moore et al.
8,196,796 B2 6/2012 Shelton, IV et al.
8,201,721 B2 6/2012 Zemlok et al.
8,205,619 B2 6/2012 Shah et al.
8,205,780 B2 6/2012 Sorrentino et al.
8,205,781 B2 6/2012 Baxter, III et al.
8,210,412 B2 7/2012 Marczyk
8,210,416 B2 7/2012 Milliman et al.
8,215,532 B2 7/2012 Marczyk
8,216,236 B2 7/2012 Heinrich et al.
8,220,688 B2 7/2012 Laurent et al.
8,220,690 B2 7/2012 Hess et al.
8,225,979 B2 7/2012 Farascioni et al.
8,231,040 B2 7/2012 Zemlok et al.
8,231,041 B2 7/2012 Marczyk et al.
8,235,272 B2 8/2012 Nicholas et al.
8,235,273 B2 8/2012 Olson et al.
8,235,274 B2 8/2012 Cappola
8,236,010 B2 8/2012 Ortiz et al.
8,240,536 B2 8/2012 Marczyk
8,240,537 B2 8/2012 Marczyk
8,241,322 B2 8/2012 Whitman et al.
8,245,897 B2 8/2012 Tzakis et al.
8,245,898 B2 8/2012 Smith et al.
8,245,899 B2 8/2012 Swensgard et al.
8,245,931 B2 8/2012 Shigeta
8,252,009 B2 8/2012 Weller et al.
8,256,653 B2 9/2012 Farascioni
8,256,654 B2 9/2012 Bettuchi et al.
8,256,655 B2 9/2012 Sniffin et al.
8,256,656 B2 9/2012 Milliman et al.
8,267,300 B2 9/2012 Boudreaux
8,272,551 B2 9/2012 Knodel et al.
8,272,553 B2 9/2012 Mastri et al.
8,272,554 B2 9/2012 Whitman et al.
8,276,594 B2 10/2012 Shah
8,276,801 B2 10/2012 Zemlok et al.
8,281,973 B2 10/2012 Wenchell et al.
8,286,847 B2 10/2012 Taylor
8,286,848 B2 10/2012 Wenchell et al.
8,286,850 B2 10/2012 Viola
8,292,146 B2 10/2012 Holsten et al.
8,292,147 B2 10/2012 Viola
8,292,148 B2 10/2012 Viola
8,292,149 B2 10/2012 Ivanko
8,292,150 B2 10/2012 Bryant
8,292,151 B2 10/2012 Viola
8,292,152 B2 10/2012 Milliman et al.
8,292,153 B2 10/2012 Jankowski

(56) References Cited

U.S. PATENT DOCUMENTS

| | | | |
|---|---|---|---|
| 8,292,154 | B2 | 10/2012 | Marczyk |
| 8,292,155 | B2 | 10/2012 | Shelton, IV et al. |
| 8,292,156 | B2 | 10/2012 | Kostrzewski |
| 8,292,158 | B2 | 10/2012 | Sapienza |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,044 | B2 | 11/2012 | Viola |
| 8,308,046 | B2 | 11/2012 | Prommersberger |
| 8,308,757 | B2 | 11/2012 | Hillstead et al. |
| 8,317,070 | B2 | 11/2012 | Hueil et al. |
| 8,317,071 | B1 | 11/2012 | Knodel |
| 8,322,455 | B2 | 12/2012 | Shelton, IV et al. |
| 8,322,589 | B2 | 12/2012 | Boudreaux |
| 8,328,061 | B2 | 12/2012 | Kasvikis |
| 8,328,065 | B2 | 12/2012 | Shah |
| 8,333,313 | B2 | 12/2012 | Boudreaux et al. |
| 8,336,751 | B2 | 12/2012 | Scirica |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,353,437 | B2 | 1/2013 | Boudreaux |
| 8,353,440 | B2 | 1/2013 | Whitman et al. |
| 8,356,740 | B1 | 1/2013 | Knodel |
| 8,357,174 | B2 | 1/2013 | Roth et al. |
| 8,360,294 | B2 | 1/2013 | Scirica |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,365,971 | B1 | 2/2013 | Knodel |
| 8,365,972 | B2 | 2/2013 | Aranyi et al. |
| 8,365,973 | B1 | 2/2013 | White et al. |
| 8,365,976 | B2 | 2/2013 | Hess et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,381,828 | B2 | 2/2013 | Whitman et al. |
| 8,381,961 | B2 | 2/2013 | Holsten et al. |
| 8,387,848 | B2 | 3/2013 | Johnson et al. |
| 8,387,849 | B2 | 3/2013 | Buesseler et al. |
| 8,387,850 | B2 | 3/2013 | Hathaway et al. |
| 8,388,652 | B2 | 3/2013 | Viola |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,397,971 | B2 | 3/2013 | Yates et al. |
| 8,397,972 | B2 | 3/2013 | Kostrzewski |
| 8,403,195 | B2 | 3/2013 | Beardsley et al. |
| 8,403,196 | B2 | 3/2013 | Beardsley et al. |
| 8,403,197 | B2 | 3/2013 | Vidal et al. |
| 8,403,198 | B2 | 3/2013 | Sorrentino et al. |
| 8,403,956 | B1 | 3/2013 | Thompson et al. |
| 8,408,439 | B2 | 4/2013 | Huang et al. |
| 8,408,440 | B2 | 4/2013 | Olson et al. |
| 8,408,442 | B2 | 4/2013 | Racenet et al. |
| 8,413,868 | B2 | 4/2013 | Cappola |
| 8,413,869 | B2 | 4/2013 | Heinrich |
| 8,413,871 | B2 | 4/2013 | Racenet et al. |
| 8,418,904 | B2 | 4/2013 | Wenchell et al. |
| 8,418,905 | B2 | 4/2013 | Milliman |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,419,768 | B2 | 4/2013 | Marczyk |
| 8,424,735 | B2 | 4/2013 | Viola et al. |
| 8,424,736 | B2 | 4/2013 | Scirica et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,439,244 | B2 | 5/2013 | Holcomb et al. |
| 8,439,245 | B2 | 5/2013 | Knodel et al. |
| 8,439,246 | B1 | 5/2013 | Knodel |
| 8,444,036 | B2 | 5/2013 | Shelton, IV |
| 8,444,037 | B2 | 5/2013 | Nicholas et al. |
| 8,444,038 | B2 | 5/2013 | Farascioni et al. |
| 8,448,832 | B2 | 5/2013 | Viola et al. |
| 8,453,652 | B2 | 6/2013 | Stopek |
| 8,453,905 | B2 | 6/2013 | Holcomb et al. |
| 8,453,906 | B2 | 6/2013 | Huang et al. |
| 8,453,907 | B2 | 6/2013 | Laurent et al. |
| 8,453,908 | B2 | 6/2013 | Bedi et al. |
| 8,453,909 | B2 | 6/2013 | Olson et al. |
| 8,453,910 | B2 | 6/2013 | Bettuchi et al. |
| 8,453,912 | B2 | 6/2013 | Mastri et al. |
| 8,453,913 | B2 | 6/2013 | Milliman |
| 8,453,914 | B2 | 6/2013 | Laurent et al. |
| 8,454,628 | B2 | 6/2013 | Smith et al. |
| 8,459,520 | B2 | 6/2013 | Giordano et al. |
| 8,459,521 | B2 | 6/2013 | Zemlok et al. |
| 8,459,522 | B2 | 6/2013 | Marczyk |
| 8,459,523 | B2 | 6/2013 | Whitman |
| 8,459,524 | B2 | 6/2013 | Pribanic et al. |
| 8,459,525 | B2 | 6/2013 | Yates et al. |
| 8,464,922 | B2 | 6/2013 | Marczyk |
| 8,464,923 | B2 | 6/2013 | Shelton, IV |
| 8,469,252 | B2 | 6/2013 | Holcomb et al. |
| 8,469,254 | B2 | 6/2013 | Czernik et al. |
| 8,474,677 | B2 | 7/2013 | Woodard, Jr. et al. |
| 8,479,967 | B2 | 7/2013 | Marczyk |
| 8,479,968 | B2 | 7/2013 | Hodgkinson et al. |
| 8,479,969 | B2 | 7/2013 | Shelton, IV |
| 8,485,412 | B2 | 7/2013 | Shelton, IV et al. |
| 8,490,852 | B2 | 7/2013 | Viola |
| 8,496,152 | B2 | 7/2013 | Viola |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,499,993 | B2 | 8/2013 | Shelton, IV et al. |
| 8,505,799 | B2 | 8/2013 | Viola et al. |
| 8,505,802 | B2 | 8/2013 | Viola et al. |
| 8,511,575 | B2 | 8/2013 | Cok |
| 8,512,359 | B2 | 8/2013 | Whitman et al. |
| 8,512,402 | B2 | 8/2013 | Marczyk et al. |
| 8,517,240 | B1 | 8/2013 | Mata et al. |
| 8,517,241 | B2 | 8/2013 | Nicholas et al. |
| 8,517,243 | B2 | 8/2013 | Giordano et al. |
| 8,517,244 | B2 | 8/2013 | Shelton, IV et al. |
| 8,523,041 | B2 | 9/2013 | Ishitsuki et al. |
| 8,523,042 | B2 | 9/2013 | Masiakos et al. |
| 8,523,043 | B2 | 9/2013 | Ullrich et al. |
| 8,534,528 | B2 | 9/2013 | Shelton, IV |
| 8,540,128 | B2 | 9/2013 | Shelton, IV et al. |
| 8,540,129 | B2 | 9/2013 | Baxter, III et al. |
| 8,540,130 | B2 | 9/2013 | Moore et al. |
| 8,540,131 | B2 | 9/2013 | Swayze |
| 8,540,733 | B2 | 9/2013 | Whitman et al. |
| 8,544,711 | B2 | 10/2013 | Ma et al. |
| 8,550,325 | B2 | 10/2013 | Cohen et al. |
| 8,556,151 | B2 | 10/2013 | Viola |
| 8,561,870 | B2 | 10/2013 | Baxter, III et al. |
| 8,561,873 | B2 | 10/2013 | Ingmanson et al. |
| 8,561,874 | B2 | 10/2013 | Scirica |
| 8,567,656 | B2 | 10/2013 | Shelton, IV et al. |
| 8,573,461 | B2 | 11/2013 | Shelton, IV et al. |
| 8,573,463 | B2 | 11/2013 | Scirica et al. |
| 8,573,465 | B2 | 11/2013 | Shelton, IV |
| 8,579,176 | B2 | 11/2013 | Smith et al. |
| 8,579,177 | B2 | 11/2013 | Beetel |
| 8,584,919 | B2 | 11/2013 | Hueil et al. |
| 8,584,920 | B2 | 11/2013 | Hodgkinson |
| 8,590,762 | B2 | 11/2013 | Hess et al. |
| 8,596,515 | B2 | 12/2013 | Okoniewski |

(56) References Cited

U.S. PATENT DOCUMENTS

| | | | |
|---|---|---|---|
| 8,597,311 | B2 | 12/2013 | Criscuolo et al. |
| 8,602,288 | B2 | 12/2013 | Shelton, IV et al. |
| 8,608,045 | B2 | 12/2013 | Smith et al. |
| 8,608,046 | B2 | 12/2013 | Laurent et al. |
| 8,608,047 | B2 | 12/2013 | Holsten et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,430 | B2 | 12/2013 | (Prommersberger) Stopek et al. |
| 8,627,994 | B2 | 1/2014 | Zemlok et al. |
| 8,628,544 | B2 | 1/2014 | Farascioni |
| 8,631,988 | B2 | 1/2014 | Viola |
| 8,631,989 | B2 | 1/2014 | Aranyi et al. |
| 8,631,991 | B2 | 1/2014 | Cropper et al. |
| 8,632,525 | B2 | 1/2014 | Kerr et al. |
| 8,632,535 | B2 | 1/2014 | Shelton, IV et al. |
| 8,636,187 | B2 | 1/2014 | Hueil et al. |
| 8,636,190 | B2 | 1/2014 | Zemlok et al. |
| 8,636,192 | B2 | 1/2014 | Farascioni et al. |
| 8,636,762 | B2 | 1/2014 | Whitman et al. |
| 8,636,766 | B2 | 1/2014 | Milliman et al. |
| 8,640,940 | B2 | 2/2014 | Ohdaira |
| 8,657,174 | B2 | 2/2014 | Yates et al. |
| 8,657,177 | B2 | 2/2014 | Scirica et al. |
| 8,657,178 | B2 | 2/2014 | Hueil et al. |
| 8,662,371 | B2 | 3/2014 | Viola |
| 8,668,129 | B2 | 3/2014 | Olson |
| 8,672,206 | B2 | 3/2014 | Aranyi et al. |
| 8,672,208 | B2 | 3/2014 | Hess et al. |
| 8,672,209 | B2 | 3/2014 | Crainich |
| 8,678,263 | B2 | 3/2014 | Viola |
| 8,678,990 | B2 | 3/2014 | Wazer et al. |
| 8,679,155 | B2 | 3/2014 | Knodel et al. |
| 8,684,247 | B2 | 4/2014 | Scirica et al. |
| 8,684,249 | B2 | 4/2014 | Racenet et al. |
| 8,684,253 | B2 | 4/2014 | Giordano et al. |
| 8,690,039 | B2 | 4/2014 | Beardsley et al. |
| 8,695,865 | B2 | 4/2014 | Smith et al. |
| 8,695,866 | B2 | 4/2014 | Leimbach et al. |
| 8,701,958 | B2 | 4/2014 | Shelton, IV et al. |
| 8,701,959 | B2 | 4/2014 | Shah |
| 8,701,961 | B2 | 4/2014 | Ivanko |
| 8,708,213 | B2 | 4/2014 | Shelton, IV et al. |
| 8,714,429 | B2 | 5/2014 | Demmy |
| 8,715,277 | B2 | 5/2014 | Weizman |
| 8,720,766 | B2 | 5/2014 | Hess et al. |
| 8,721,630 | B2 | 5/2014 | Ortiz et al. |
| 8,727,197 | B2 | 5/2014 | Hess et al. |
| 8,727,200 | B2 | 5/2014 | Roy |
| 8,733,612 | B2 | 5/2014 | Ma |
| 8,740,034 | B2 | 6/2014 | Morgan et al. |
| 8,740,039 | B2 | 6/2014 | Farascioni |
| 8,746,529 | B2 | 6/2014 | Shelton, IV et al. |
| 8,746,530 | B2 | 6/2014 | Giordano et al. |
| 8,746,533 | B2 | 6/2014 | Whitman |
| 8,746,534 | B2 | 6/2014 | Farascioni |
| 8,746,535 | B2 | 6/2014 | Shelton, IV et al. |
| 8,747,421 | B2 | 6/2014 | Balbierz et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |
| 8,757,465 | B2 | 6/2014 | Woodard, Jr. et al. |
| 8,758,391 | B2 | 6/2014 | Swayze et al. |
| 8,763,875 | B2 | 7/2014 | Morgan et al. |
| 8,763,876 | B2 | 7/2014 | Kostrzewski |
| 8,763,877 | B2 | 7/2014 | Schall et al. |
| 8,763,879 | B2 | 7/2014 | Shelton, IV et al. |
| 8,770,458 | B2 | 7/2014 | Scirica |
| 8,777,082 | B2 | 7/2014 | Scirica |
| 8,783,541 | B2 | 7/2014 | Shelton, IV et al. |
| 8,783,542 | B2 | 7/2014 | Riestenberg et al. |
| 8,789,737 | B2 | 7/2014 | Hodgkinson et al. |
| 8,789,738 | B2 | 7/2014 | Knodel et al. |
| 8,789,739 | B2 | 7/2014 | Swensgard |
| 8,800,838 | B2 | 8/2014 | Shelton, IV |
| 8,800,840 | B2 | 8/2014 | Jankowski |
| 8,800,841 | B2 | 8/2014 | Ellerhorst et al. |
| 8,806,973 | B2 | 8/2014 | Ross et al. |
| 8,808,311 | B2 | 8/2014 | Heinrich et al. |
| 8,814,024 | B2 | 8/2014 | Woodard, Jr. et al. |
| 8,814,025 | B2 | 8/2014 | Miller et al. |
| 8,820,603 | B2 | 9/2014 | Shelton, IV et al. |
| 8,820,605 | B2 | 9/2014 | Shelton, IV |
| 8,820,606 | B2 | 9/2014 | Hodgkinson |
| 8,820,607 | B2 | 9/2014 | Marczyk |
| 8,827,133 | B2 | 9/2014 | Shelton, IV et al. |
| 8,827,134 | B2 | 9/2014 | Viola et al. |
| 8,833,631 | B2 | 9/2014 | Munro, III et al. |
| 8,833,632 | B2 | 9/2014 | Swensgard |
| 8,840,003 | B2 | 9/2014 | Morgan et al. |
| 8,840,603 | B2 | 9/2014 | Shelton, IV et al. |
| 8,844,788 | B2 | 9/2014 | Knodel |
| 8,851,354 | B2 | 10/2014 | Swensgard et al. |
| 8,851,355 | B2 | 10/2014 | Aranyi et al. |
| 8,857,693 | B2 | 10/2014 | Schuckmann et al. |
| 8,864,007 | B2 | 10/2014 | Widenhouse et al. |
| 8,864,009 | B2 | 10/2014 | Shelton, IV et al. |
| 8,864,010 | B2 | 10/2014 | Williams |
| 8,870,050 | B2 | 10/2014 | Hodgkinson |
| 8,875,971 | B2 | 11/2014 | Hall et al. |
| 8,875,972 | B2 | 11/2014 | Weisenburgh, II et al. |
| 8,893,949 | B2 | 11/2014 | Shelton, IV et al. |
| 8,893,950 | B2 | 11/2014 | Marczyk |
| 8,899,461 | B2 | 12/2014 | Farascioni |
| 8,899,462 | B2 | 12/2014 | Kostrzewski et al. |
| 8,899,463 | B2 | 12/2014 | Schall et al. |
| 8,899,464 | B2 | 12/2014 | Hueil et al. |
| 8,900,616 | B2 | 12/2014 | Belcheva et al. |
| 8,920,435 | B2 | 12/2014 | Smith et al. |
| 8,925,782 | B2 | 1/2015 | Shelton, IV |
| 8,926,598 | B2 | 1/2015 | Mollere et al. |
| 8,931,681 | B2 | 1/2015 | Kostrzewski |
| 8,931,682 | B2 | 1/2015 | Timm et al. |
| 8,931,693 | B1 | 1/2015 | Kumar et al. |
| 8,955,732 | B2 | 2/2015 | Zemlok et al. |
| 8,958,429 | B2 | 2/2015 | Shukla et al. |
| 8,960,517 | B2 | 2/2015 | Lee |
| 8,960,520 | B2 | 2/2015 | McCuen |
| 8,967,443 | B2 | 3/2015 | McCuen |
| 8,967,446 | B2 | 3/2015 | Beardsley et al. |
| 8,973,803 | B2 | 3/2015 | Hall et al. |
| 8,978,954 | B2 | 3/2015 | Shelton, IV et al. |
| 8,978,956 | B2 | 3/2015 | Schall et al. |
| 8,991,677 | B2 | 3/2015 | Moore et al. |
| 8,991,678 | B2 | 3/2015 | Wellman et al. |
| 8,998,058 | B2 | 4/2015 | Moore et al. |
| 8,998,060 | B2 | 4/2015 | Bruewer et al. |
| 9,005,230 | B2 | 4/2015 | Yates et al. |
| 9,010,606 | B2 | 4/2015 | Aranyi et al. |
| 9,010,607 | B2 | 4/2015 | Kostrzewski |
| 9,010,610 | B2 | 4/2015 | Hodgkinson |
| 9,016,539 | B2 | 4/2015 | Kostrzewski et al. |
| 9,016,541 | B2 | 4/2015 | Viola et al. |
| 9,016,542 | B2 | 4/2015 | Shelton, IV et al. |
| 9,016,544 | B2 | 4/2015 | Hodgkinson et al. |
| 9,016,545 | B2 | 4/2015 | Aranyi et al. |
| 9,016,546 | B2 | 4/2015 | Demmy et al. |
| 9,017,371 | B2 | 4/2015 | Whitman et al. |
| 9,022,271 | B2 | 5/2015 | Scirica |
| 9,027,817 | B2 | 5/2015 | Milliman et al. |
| 9,033,203 | B2 | 5/2015 | Woodard, Jr. et al. |
| 9,044,228 | B2 | 6/2015 | Woodard, Jr. et al. |
| 9,044,229 | B2 | 6/2015 | Scheib et al. |
| 9,050,084 | B2 | 6/2015 | Schmid et al. |
| 9,055,941 | B2 | 6/2015 | Schmid et al. |
| 9,060,770 | B2 | 6/2015 | Shelton, IV et al. |
| 9,072,535 | B2 | 7/2015 | Shelton, IV et al. |
| 9,084,601 | B2 | 7/2015 | Moore et al. |
| 9,084,602 | B2 | 7/2015 | Gleiman |
| 9,089,326 | B2 | 7/2015 | Krumanaker et al. |
| 9,095,339 | B2 | 8/2015 | Moore et al. |
| 9,101,359 | B2 | 8/2015 | Smith et al. |
| 9,107,663 | B2 | 8/2015 | Swensgard |
| 9,107,664 | B2 | 8/2015 | Marczyk |

(56) References Cited

U.S. PATENT DOCUMENTS 9,107,667 B2 8/2015 Hodgkinson
9,113,862 B2 8/2015 Morgan et al.
9,113,864 B2 8/2015 Morgan et al.
9,113,870 B2 8/2015 Viola
9,113,872 B2 8/2015 Viola
9,113,880 B2 8/2015 Zemlok et al.
9,125,649 B2 9/2015 Bruewer et al.
9,138,225 B2 9/2015 Huang et al.
9,155,537 B2 10/2015 Katre et al.
9,179,912 B2 11/2015 Yates et al.
9,192,378 B2 11/2015 Aranyi et al.
9,192,379 B2 11/2015 Aranyi et al.
9,192,384 B2 11/2015 Bettuchi
9,198,644 B2 12/2015 Balek et al.
9,198,660 B2 12/2015 Hodgkinson
9,198,661 B2 12/2015 Swensgard
9,198,662 B2 12/2015 Barton et al.
9,204,876 B2 12/2015 Cappola et al.
9,204,877 B2 12/2015 Whitman et al.
9,204,880 B2 12/2015 Baxter, III et al.
9,216,019 B2 12/2015 Schmid et al.
9,216,020 B2 12/2015 Zhang et al.
9,220,500 B2 12/2015 Swayze et al.
9,220,501 B2 12/2015 Baxter, III et al.
9,220,502 B2 12/2015 Zemlok et al.
9,232,941 B2 1/2016 Mandakolathur Vasudevan et al.
9,232,944 B2 1/2016 Cappola et al.
9,237,891 B2 1/2016 Shelton, IV
9,237,892 B2 1/2016 Hodgkinson
9,254,180 B2 2/2016 Huitema et al.
9,265,585 B2 2/2016 Wingardner et al.
9,271,728 B2 3/2016 Gupta et al.
9,272,406 B2 3/2016 Aronhalt et al.
9,277,919 B2 3/2016 Timmer et al.
9,282,962 B2 3/2016 Schmid et al.
9,283,054 B2 3/2016 Morgan et al.
9,289,209 B2 3/2016 Gurumurthy et al.
9,289,210 B2 3/2016 Baxter, III et al.
9,289,225 B2 3/2016 Shelton, IV et al.
9,295,464 B2 3/2016 Shelton, IV et al.
9,295,465 B2 3/2016 Farascioni
9,295,466 B2 3/2016 Hodgkinson et al.
9,301,752 B2 4/2016 Mandakolathur Vasudevan et al.
9,301,753 B2 4/2016 Aldridge et al.
9,301,757 B2 4/2016 Williams
9,301,759 B2 4/2016 Spivey et al.
9,307,965 B2 4/2016 Ming et al.
9,307,986 B2 4/2016 Hall et al.
9,307,989 B2 4/2016 Shelton, IV et al.
9,314,246 B2 4/2016 Shelton, IV et al.
9,320,518 B2 4/2016 Henderson et al.
9,320,521 B2 4/2016 Shelton, IV et al.
9,320,523 B2 4/2016 Shelton, IV et al.
9,326,767 B2 5/2016 Koch, Jr. et al.
9,326,771 B2 5/2016 Baxter, III et al.
9,332,987 B2 5/2016 Leimbach et al.
9,345,477 B2 5/2016 Anim et al.
9,345,478 B2 5/2016 Knodel
9,345,479 B2 5/2016 (Tarinelli) Racenet et al.
9,345,481 B2 5/2016 Hall et al.
9,345,780 B2 5/2016 Manoharan et al.
9,351,726 B2 5/2016 Leimbach
9,351,727 B2 5/2016 Leimbach et al.
9,351,732 B2 5/2016 Hodgkinson
9,358,003 B2 6/2016 Hall et al.
9,364,217 B2 6/2016 Kostrzewski et al.
9,364,218 B2 6/2016 Scirica
9,364,219 B2 6/2016 Olson et al.
9,364,220 B2 6/2016 Williams
9,364,227 B2 6/2016 Kostrzewski
9,364,231 B2 6/2016 Wenchell
9,364,233 B2 6/2016 Alexander, III et al.
9,370,358 B2 6/2016 Shelton, IV et al.
9,370,362 B2 6/2016 Petty et al.
9,386,983 B2 7/2016 Swensgard et al.
9,386,984 B2 7/2016 Aronhalt et al.
9,386,988 B2 7/2016 Baxter, III et al.
9,393,018 B2 7/2016 Wang et al.
9,398,911 B2 7/2016 Auld
9,402,604 B2 8/2016 Williams et al.
9,402,627 B2 8/2016 Stevenson et al.
9,421,014 B2 8/2016 Ingmanson et al.
9,433,419 B2 9/2016 Gonzalez et al.
9,433,420 B2 9/2016 Hodgkinson
9,445,810 B2 9/2016 Cappola
9,445,813 B2 9/2016 Shelton, IV et al.
9,451,959 B2 9/2016 Patankar et al.
9,468,438 B2 10/2016 Baber et al.
9,468,439 B2 10/2016 Cappola et al.
9,480,476 B2 11/2016 Aldridge et al.
9,480,492 B2 11/2016 Aranyi et al.
9,492,171 B2 11/2016 Patenaude
9,498,212 B2 11/2016 Racenet et al.
9,498,219 B2 11/2016 Moore et al.
9,510,827 B2 12/2016 Kostrzewski
9,517,065 B2 12/2016 Simms et al.
9,517,066 B2 12/2016 Racenet et al.
9,522,002 B2 12/2016 Chowaniec et al.
9,539,007 B2 1/2017 Dhakad et al.
9,549,735 B2 1/2017 Shelton, IV et al.
9,554,794 B2 1/2017 Baber
9,561,029 B2 2/2017 Scheib et al.
9,561,031 B2 2/2017 Heinrich et al.
9,566,065 B2 2/2017 Knodel
9,572,576 B2 2/2017 Hodgkinson et al.
9,579,101 B2 2/2017 Whitman et al.
9,585,657 B2 3/2017 Shelton, IV et al.
9,585,662 B2 3/2017 Shelton, IV et al.
9,597,077 B2 3/2017 Hodgkinson
9,610,080 B2 4/2017 Whitfield et al.
9,615,825 B2 4/2017 Viola
9,615,826 B2 4/2017 Shelton, IV et al.
9,622,746 B2 4/2017 Simms
9,629,623 B2 4/2017 Lytle, IV et al.
9,629,626 B2 4/2017 Soltz et al.
9,629,628 B2 * 4/2017 Aranyi ............ A61B 17/07207
9,629,629 B2 4/2017 Leimbach et al.
9,642,620 B2 5/2017 Baxter, III
9,649,109 B2 5/2017 Ranucci et al.
9,655,613 B2 5/2017 Schaller
9,662,108 B2 5/2017 Williams
9,668,728 B2 6/2017 Williams et al.
9,668,732 B2 6/2017 Patel et al.
9,675,351 B2 6/2017 Hodgkinson et al.
9,681,870 B2 6/2017 Baxter, III et al.
9,687,230 B2 6/2017 Leimbach et al.
9,687,233 B2 6/2017 Fernandez et al.
9,693,772 B2 7/2017 Ingmanson et al.
9,700,309 B2 7/2017 Jaworek
9,700,319 B2 7/2017 Motooka et al.
9,706,993 B2 7/2017 Hessler et al.
9,713,470 B2 7/2017 Scirica et al.
9,713,474 B2 7/2017 Lorenz
9,717,497 B2 8/2017 Zerkle et al.
9,717,498 B2 8/2017 Aranyi et al.
9,724,092 B2 8/2017 Baxter, III et al.
9,724,095 B2 8/2017 Gupta et al.
9,763,662 B2 9/2017 Shelton, IV et al.
9,770,245 B2 9/2017 Swayze et al.
9,775,610 B2 10/2017 Nicholas et al.
9,775,635 B2 10/2017 Takei
9,782,169 B2 10/2017 Kimsey
9,782,173 B2 10/2017 Mozdzierz
9,795,379 B2 10/2017 Leimbach et al.
9,795,384 B2 10/2017 Weaner et al.
9,808,246 B2 11/2017 Shelton, IV
9,808,248 B2 11/2017 Hoffman
9,808,249 B2 11/2017 Shelton, IV
9,820,741 B2 11/2017 Kostrzewski
9,820,742 B2 11/2017 Covach et al.
9,827,002 B2 11/2017 Hausen et al.
9,839,420 B2 12/2017 Shelton, IV
9,839,421 B2 12/2017 Zerkle et al.
9,839,428 B2 12/2017 Baxter, III et al.

(56) References Cited

U.S. PATENT DOCUMENTS

| | | | | |
|---|---|---|---|---|
| 9,855,038 | B2 | 1/2018 | Smith et al. | |
| 9,855,040 | B2 | 1/2018 | Kostrzewski | |
| 9,861,358 | B2 | 1/2018 | Marczyk et al. | |
| 9,861,359 | B2 | 1/2018 | Shelton, IV et al. | |
| 9,867,612 | B2 | 1/2018 | Parihar et al. | |
| 9,867,613 | B2 | 1/2018 | Marczyk et al. | |
| 9,867,615 | B2 | 1/2018 | Fanelli et al. | |
| 9,872,683 | B2 | 1/2018 | Hopkins | |
| 9,883,860 | B2 | 2/2018 | Leimbach et al. | |
| 9,901,342 | B2 | 2/2018 | Shelton, IV et al. | |
| 9,913,646 | B2 | 3/2018 | Shelton, IV | |
| 9,918,714 | B2 | 3/2018 | Gibbons, Jr. | |
| 9,918,717 | B2 | 3/2018 | Czernik | |
| 9,924,941 | B2 | 3/2018 | Burbank | |
| 9,924,942 | B2 | 3/2018 | Swayze et al. | |
| 9,936,951 | B2 | 4/2018 | Hufnagel et al. | |
| 9,936,954 | B2 | 4/2018 | Shelton, IV et al. | |
| 9,943,311 | B2 | 4/2018 | Scirica et al. | |
| 9,949,737 | B2 | 4/2018 | Zergiebel et al. | |
| 9,955,966 | B2 | 5/2018 | Zergiebel | |
| 9,968,354 | B2 | 5/2018 | Shelton, IV et al. | |
| 9,980,724 | B2 | 5/2018 | Farascioni et al. | |
| 9,987,012 | B2 | 6/2018 | Shah | |
| 9,987,099 | B2 | 6/2018 | Chen et al. | |
| 9,993,248 | B2 | 6/2018 | Shelton, IV et al. | |
| 9,993,258 | B2 | 6/2018 | Shelton, IV et al. | |
| 10,004,497 | B2 | 6/2018 | Overmyer et al. | |
| 10,004,505 | B2 | 6/2018 | Moore et al. | |
| 10,034,668 | B2 | 7/2018 | Ebner | |
| 10,039,532 | B2 | 8/2018 | Srinivas et al. | |
| 10,039,545 | B2 | 8/2018 | Sadowski et al. | |
| 10,045,782 | B2 | 8/2018 | Murthy Aravalli | |
| 10,052,044 | B2 | 8/2018 | Shelton, IV et al. | |
| 10,058,963 | B2 | 8/2018 | Shelton, IV et al. | |
| 10,064,622 | B2 | 9/2018 | Murthy Aravalli | |
| 10,076,325 | B2 | 9/2018 | Huang et al. | |
| 10,085,750 | B2 | 10/2018 | Zergiebel et al. | |
| 10,092,290 | B2 | 10/2018 | Yigit et al. | |
| 10,092,292 | B2 | 10/2018 | Boudreaux et al. | |
| 10,111,657 | B2 | 10/2018 | McCuen | |
| 10,111,665 | B2 | 10/2018 | Aranyi | |
| 10,117,650 | B2 | 11/2018 | Nicholas et al. | |
| 10,117,654 | B2 | 11/2018 | Ingmanson et al. | |
| 10,123,796 | B2 | 11/2018 | Westling et al. | |
| 10,123,798 | B2 | 11/2018 | Baxter, III et al. | |
| 10,135,242 | B2 | 11/2018 | Baber et al. | |
| 10,143,474 | B2 | 12/2018 | Bucciaglia et al. | |
| 10,172,612 | B2 | 1/2019 | Frushour | |
| 10,172,615 | B2 | 1/2019 | Marczyk et al. | |
| 10,172,617 | B2 | 1/2019 | Shelton, IV et al. | |
| 10,175,127 | B2 | 1/2019 | Collins et al. | |
| 10,180,463 | B2 | 1/2019 | Beckman et al. | |
| 10,182,816 | B2 | 1/2019 | Shelton, IV et al. | |
| 10,206,677 | B2 | 2/2019 | Harris et al. | |
| 10,213,201 | B2 | 2/2019 | Shelton, IV et al. | |
| 10,219,804 | B2 | 3/2019 | Linder et al. | |
| 10,226,239 | B2 | 3/2019 | Nicholas et al. | |
| 10,226,250 | B2 | 3/2019 | Beckman et al. | |
| 10,226,254 | B2 | 3/2019 | Cabrera et al. | |
| 10,245,033 | B2 | 4/2019 | Overmyer et al. | |
| 10,245,036 | B1 * | 4/2019 | Schaller | A61B 17/07207 |
| 10,245,038 | B2 | 4/2019 | Hopkins et al. | |
| 10,251,725 | B2 | 4/2019 | Valentine et al. | |
| 10,265,065 | B2 | 4/2019 | Shelton, IV et al. | |
| 10,265,066 | B2 | 4/2019 | Measamer et al. | |
| 10,265,074 | B2 | 4/2019 | Shelton, IV et al. | |
| 10,271,840 | B2 | 4/2019 | Sapre | |
| 10,271,841 | B2 | 4/2019 | Overmyer et al. | |
| 10,285,694 | B2 | 5/2019 | Viola et al. | |
| 10,285,698 | B2 | 5/2019 | Cappola et al. | |
| 10,321,907 | B2 | 6/2019 | Shelton, IV et al. | |
| 10,327,776 | B2 | 6/2019 | Harris et al. | |
| 10,335,150 | B2 | 7/2019 | Shelton, IV | |
| 10,349,939 | B2 | 7/2019 | Shelton, IV et al. | |
| 10,349,941 | B2 | 7/2019 | Marczyk et al. | |
| 10,390,823 | B2 | 8/2019 | Shelton, IV et al. | |
| 10,390,825 | B2 | 8/2019 | Shelton, IV et al. | |
| 10,390,828 | B2 | 8/2019 | Vendely et al. | |
| 10,405,857 | B2 | 9/2019 | Shelton | |
| 10,426,468 | B2 | 10/2019 | Contini et al. | |
| 10,441,279 | B2 | 10/2019 | Shelton, IV et al. | |
| 10,456,129 | B2 | 10/2019 | Shelton, IV et al. | |
| 10,456,130 | B2 | 10/2019 | Cheney et al. | |
| 10,463,368 | B2 | 11/2019 | Kostrzewski | |
| 10,470,762 | B2 | 11/2019 | Leimbach et al. | |
| 10,470,911 | B2 | 11/2019 | Thompson et al. | |
| 10,478,182 | B2 | 11/2019 | Taylor | |
| 10,478,183 | B2 | 11/2019 | Hess et al. | |
| 10,478,187 | B2 | 11/2019 | Shelton, IV et al. | |
| 10,524,785 | B2 * | 1/2020 | Zemlok | A61B 17/07207 |
| 10,542,976 | B2 | 1/2020 | Calderoni et al. | |
| 10,548,504 | B2 | 2/2020 | Shelton, IV et al. | |
| 10,548,593 | B2 | 2/2020 | Shelton, IV et al. | |
| 10,548,599 | B2 | 2/2020 | Marczyk et al. | |
| 10,561,417 | B2 | 2/2020 | Zergiebel et al. | |
| 10,561,418 | B2 | 2/2020 | Richard et al. | |
| 10,568,621 | B2 | 2/2020 | Shelton, IV et al. | |
| 10,588,629 | B2 | 3/2020 | Malinouskas et al. | |
| 10,595,929 | B2 | 3/2020 | Boudreaux et al. | |
| 10,603,035 | B2 | 3/2020 | Beardsley | |
| 10,603,128 | B2 | 3/2020 | Zergiebel et al. | |
| 10,617,412 | B2 | 4/2020 | Shelton, IV et al. | |
| 10,624,634 | B2 | 4/2020 | Shelton, IV et al. | |
| 10,667,806 | B2 | 6/2020 | Schneider | |
| 10,687,806 | B2 | 6/2020 | Shelton, IV et al. | |
| 10,695,053 | B2 | 6/2020 | Hess et al. | |
| 10,779,822 | B2 | 9/2020 | Yates et al. | |
| 10,792,038 | B2 | 10/2020 | Becerra et al. | |
| 10,799,238 | B2 * | 10/2020 | Zemlok | A61B 17/068 |
| 10,828,030 | B2 | 11/2020 | Weir et al. | |
| 10,863,984 | B2 | 12/2020 | Shelton, IV et al. | |
| 11,241,228 | B2 * | 2/2022 | Nicholas | A61B 17/072 |
| 11,278,280 | B2 * | 3/2022 | Shelton, IV | A61B 17/072 |
| 11,337,692 | B2 * | 5/2022 | Aranyi | A61B 17/07207 |
| 11,464,509 | B2 | 10/2022 | Zemlok | |
| 11,464,511 | B2 * | 10/2022 | Timm | A61B 17/29 |
| 11,576,671 | B1 * | 2/2023 | Williams | A61B 17/0686 |
| 11,730,475 | B2 * | 8/2023 | Hudson | A61B 90/98 227/175.1 |
| 11,759,224 | B2 * | 9/2023 | Shelton, IV | A61B 17/29 606/143 |
| 11,896,220 | B2 | 2/2024 | Williams | |
| 12,011,164 | B2 * | 6/2024 | Shelton, IV | A61B 17/072 |
| 2003/0083656 | A1 * | 5/2003 | Morrison | A61B 18/1492 606/45 |
| 2004/0108357 | A1 | 6/2004 | Milliman et al. | |
| 2004/0199180 | A1 | 10/2004 | Knodel et al. | |
| 2004/0199181 | A1 | 10/2004 | Knodel et al. | |
| 2004/0232195 | A1 * | 11/2004 | Shelton, IV | A61B 17/07207 227/180.1 |
| 2004/0232200 | A1 * | 11/2004 | Shelton, IV | A61B 17/07207 227/176.1 |
| 2004/0243151 | A1 | 12/2004 | Demmy et al. | |
| 2004/0267310 | A1 | 12/2004 | Racenet et al. | |
| 2005/0216055 | A1 | 9/2005 | Scirica et al. | |
| 2006/0049229 | A1 | 3/2006 | Milliman et al. | |
| 2006/0180634 | A1 | 8/2006 | Shelton et al. | |
| 2006/0289602 | A1 | 12/2006 | Wales et al. | |
| 2007/0073341 | A1 | 3/2007 | Smith et al. | |
| 2007/0084897 | A1 | 4/2007 | Shelton et al. | |
| 2007/0102472 | A1 | 5/2007 | Shelton | |
| 2007/0102475 | A1 * | 5/2007 | Ortiz | A61B 17/07207 227/19 |
| 2007/0106317 | A1 | 5/2007 | Shelton, IV | |
| 2007/0119901 | A1 | 5/2007 | Ehrenfels et al. | |
| 2007/0145096 | A1 | 6/2007 | Viola et al. | |
| 2007/0170225 | A1 | 7/2007 | Shelton et al. | |
| 2007/0175950 | A1 | 8/2007 | Shelton et al. | |
| 2007/0175951 | A1 | 8/2007 | Shelton et al. | |
| 2007/0175955 | A1 | 8/2007 | Shelton et al. | |
| 2007/0194079 | A1 | 8/2007 | Hueil et al. | |
| 2007/0194082 | A1 | 8/2007 | Morgan et al. | |
| 2008/0029570 | A1 | 2/2008 | Shelton et al. | |
| 2008/0029573 | A1 | 2/2008 | Shelton et al. | |

(56) References Cited

U.S. PATENT DOCUMENTS

2008/0029574 A1 2/2008 Shelton et al.
2008/0029575 A1 2/2008 Shelton et al.
2008/0078802 A1 4/2008 Hess et al.
2008/0110961 A1 5/2008 Voegele et al.
2008/0169328 A1 7/2008 Shelton
2008/0169332 A1 7/2008 Shelton et al.
2008/0169333 A1 7/2008 Shelton et al.
2008/0251568 A1 10/2008 Zemlok et al.
2008/0255418 A1* 10/2008 Zemlok ................ A61B 17/072 600/118
2008/0287987 A1 11/2008 Boyden et al.
2008/0296346 A1 12/2008 Shelton, IV et al.
2008/0308602 A1 12/2008 Timm et al.
2008/0308603 A1 12/2008 Shelton et al.
2009/0001121 A1 1/2009 Hess et al.
2009/0001130 A1 1/2009 Hess et al.
2009/0090763 A1 4/2009 Zemlok et al.
2009/0090766 A1 4/2009 Knodel
2009/0242610 A1 10/2009 Shelton, IV et al.
2009/0255974 A1 10/2009 Viola
2009/0270893 A1* 10/2009 Arcenio ........... A61B 17/32002 606/170
2009/0308907 A1 12/2009 Nalagatla et al.
2010/0012703 A1 1/2010 Calabrese et al.
2010/0065604 A1* 3/2010 Weng ............... A61B 17/07207 227/180.1
2010/0069942 A1 3/2010 Shelton, IV
2010/0127041 A1 5/2010 Morgan et al.
2010/0133317 A1 6/2010 Shelton, IV et al.
2010/0147921 A1 6/2010 Olson
2010/0147922 A1 6/2010 Olson
2010/0155453 A1 6/2010 Bombard et al.
2010/0193566 A1 8/2010 Scheib et al.
2010/0224668 A1 9/2010 Fontayne et al.
2010/0249802 A1 9/2010 May et al.
2010/0252611 A1 10/2010 Ezzat et al.
2011/0006101 A1 1/2011 Hall et al.
2011/0024477 A1 2/2011 Hall
2011/0024478 A1 2/2011 Shelton, IV
2011/0036891 A1 2/2011 Zemlok et al.
2011/0087276 A1 4/2011 Bedi et al.
2011/0101069 A1 5/2011 Bombard et al.
2011/0139851 A1* 6/2011 McCuen .......... A61B 17/07207 227/175.1
2011/0147433 A1 6/2011 Shelton, IV et al.
2011/0163146 A1 7/2011 Ortiz et al.
2011/0192882 A1 8/2011 Hess et al.
2011/0204119 A1* 8/2011 McCuen .............. A61B 17/068 227/175.1
2011/0278343 A1 11/2011 Knodel et al.
2011/0290856 A1 12/2011 Shelton, IV et al.
2012/0053406 A1 3/2012 Conlon et al.
2012/0061446 A1 3/2012 Knodel et al.
2012/0074200 A1 3/2012 Schmid et al.
2012/0080478 A1 4/2012 Morgan et al.
2012/0080495 A1 4/2012 Holcomb et al.
2012/0080498 A1 4/2012 Shelton, IV et al.
2012/0091183 A1 4/2012 Manoux et al.
2012/0116416 A1 5/2012 Neff et al.
2012/0138659 A1 6/2012 Marczyk et al.
2012/0193394 A1 8/2012 Holcomb et al.
2012/0193399 A1 8/2012 Holcomb et al.
2012/0211542 A1 8/2012 Racenet
2012/0228358 A1 9/2012 Zemlok et al.
2012/0234895 A1 9/2012 O'Connor et al.
2012/0234897 A1 9/2012 Shelton, IV et al.
2012/0241504 A1 9/2012 Soltz et al.
2012/0248169 A1 10/2012 Widenhouse et al.
2012/0286022 A1 11/2012 Olson et al.
2012/0298722 A1 11/2012 Hess et al.
2013/0008937 A1 1/2013 Viola
2013/0012983 A1 1/2013 Kleyman
2013/0020375 A1 1/2013 Shelton, IV et al.
2013/0020376 A1 1/2013 Shelton, IV et al.
2013/0026208 A1 1/2013 Shelton, IV et al.
2013/0026210 A1 1/2013 Shelton, IV et al.
2013/0041406 A1 2/2013 Bear et al.
2013/0068816 A1 3/2013 Mandakolathur Vasudevan et al.
2013/0068818 A1 3/2013 Kasvikis
2013/0075447 A1 3/2013 Weisenburgh, II et al.
2013/0098970 A1 4/2013 Racenet et al.
2013/0153641 A1 6/2013 Shelton, IV et al.
2013/0175316 A1 7/2013 Thompson et al.
2013/0256380 A1 10/2013 Schmid et al.
2013/0277410 A1 10/2013 Fernandez et al.
2013/0334280 A1 12/2013 Krehel et al.
2014/0005662 A1* 1/2014 Shelton, IV ....... A61B 18/1445 606/41
2014/0014704 A1 1/2014 Onukuri et al.
2014/0014707 A1 1/2014 Onukuri et al.
2014/0048580 A1 2/2014 Merchant et al.
2014/0166724 A1 6/2014 Schellin et al.
2014/0166725 A1 6/2014 Schellin et al.
2014/0166726 A1 6/2014 Schellin et al.
2014/0175150 A1 6/2014 Shelton, IV et al.
2014/0224686 A1* 8/2014 Aronhalt ............ A61B 17/0682 206/339
2014/0239047 A1 8/2014 Hodgkinson et al.
2014/0246475 A1 9/2014 Hall et al.
2014/0252064 A1 9/2014 Mozdzierz et al.
2014/0263541 A1 9/2014 Leimbach et al.
2014/0263552 A1 9/2014 Hall et al.
2014/0263558 A1 9/2014 Hausen et al.
2014/0284371 A1 9/2014 Morgan et al.
2014/0291379 A1 10/2014 Schellin et al.
2014/0291383 A1 10/2014 Spivey et al.
2014/0358129 A1* 12/2014 Zergiebel ............... A61B 17/28 606/1
2014/0367445 A1 12/2014 Ingmanson et al.
2015/0076211 A1 3/2015 Irka et al.
2015/0080924 A1* 3/2015 Stulen ............ A61B 17/320092 606/169
2015/0127022 A1* 5/2015 Whitfield ............... A61B 17/10 606/143
2015/0134076 A1 5/2015 Shelton, IV et al.
2015/0173746 A1* 6/2015 Baxter, III ....... A61B 17/07207 227/176.1
2015/0173749 A1 6/2015 Shelton, IV et al.
2015/0173756 A1 6/2015 Baxter, III et al.
2015/0250474 A1 9/2015 Abbott et al.
2015/0272557 A1 10/2015 Overmyer et al.
2015/0272576 A1* 10/2015 Cappola ............... A61B 17/072 227/175.2
2015/0297222 A1 10/2015 Huitema et al.
2015/0297225 A1 10/2015 Huitema et al.
2015/0316431 A1* 11/2015 Collins ................. G01L 5/0028 227/176.1
2015/0374363 A1* 12/2015 Laurent, IV ......... A61B 17/105 227/176.1
2015/0374372 A1 12/2015 Zergiebel et al.
2016/0066909 A1 3/2016 Baber et al.
2016/0157863 A1* 6/2016 Williams ............. A61B 17/068 227/175.2
2016/0166249 A1 6/2016 Knodel
2016/0166253 A1 6/2016 Knodel
2016/0235494 A1 8/2016 Shelton, IV et al.
2016/0302791 A1 10/2016 Schmitt
2016/0354176 A1 12/2016 Schmitt
2016/0367256 A1* 12/2016 Hensel ................. A61B 17/105
2017/0000483 A1 1/2017 Motai et al.
2017/0164945 A1* 6/2017 Chowaniec ...... A61B 17/07207
2017/0281171 A1* 10/2017 Shelton, IV ......... A61B 17/115
2017/0281188 A1* 10/2017 Shelton, IV ..... A61B 17/07207
2017/0290584 A1* 10/2017 Jasemian ............. A61B 17/072
2017/0296190 A1* 10/2017 Aronhalt .............. A61B 17/105
2018/0028271 A1* 2/2018 Rockrohr ............... A61B 34/35
2018/0153550 A1* 6/2018 Souls ............... A61B 17/00234
2018/0168646 A1* 6/2018 Shelton, IV ..... A61B 17/07292
2018/0317913 A1* 11/2018 Beardsley ........ A61B 17/07207
2018/0353185 A1* 12/2018 Nicholas ............ A61B 17/1155
2018/0360454 A1* 12/2018 Shelton, IV ......... A61B 17/105
2019/0000477 A1* 1/2019 Shelton, IV ....... A61B 18/1442

(56) References Cited

U.S. PATENT DOCUMENTS

| | | | | |
|---|---|---|---|---|
| 2019/0069895 | A1* | 3/2019 | Satti, III | A61B 17/10 |
| 2019/0099181 | A1* | 4/2019 | Shelton, IV | A61B 17/0682 |
| 2019/0183503 | A1* | 6/2019 | Shelton, IV | A61B 90/06 |
| 2019/0192158 | A1* | 6/2019 | Scott | A61B 17/07207 |
| 2019/0201027 | A1* | 7/2019 | Shelton, IV | A61B 17/320068 |
| 2019/0201137 | A1* | 7/2019 | Shelton, IV | G16H 50/20 |
| 2019/0240040 | A1* | 8/2019 | Al-Jazaeri | A61B 17/1671 |
| 2019/0298356 | A1* | 10/2019 | Shelton, IV | A61B 17/07207 |
| 2019/0308330 | A1* | 10/2019 | Regnier | B25J 15/02 |
| 2020/0138463 | A1* | 5/2020 | Kostrzewski | A61B 17/07292 |
| 2020/0205818 | A1* | 7/2020 | Beardsley | A61B 17/072 |
| 2021/0022594 | A1* | 1/2021 | Jen | A61F 2/9517 |
| 2021/0282770 | A1* | 9/2021 | Fernandes | A61B 17/07207 |
| 2022/0015845 | A1* | 1/2022 | Beckman | A61B 34/30 |
| 2022/0133310 | A1* | 5/2022 | Ross | A61B 17/072 227/176.1 |
| 2022/0226054 | A1* | 7/2022 | Beckman | A61B 17/07207 |
| 2022/0378423 | A1* | 12/2022 | Chowaniec | A61B 17/07207 |
| 2023/0181187 | A1 | 6/2023 | Williams | |
| 2023/0263522 | A1* | 8/2023 | Zhang | A61B 17/07207 227/175.1 |
| 2024/0382201 | A1* | 11/2024 | Scott | A61B 17/07207 |

FOREIGN PATENT DOCUMENTS

| | | | |
|---|---|---|---|
| CA | 2884962 | A1 | 11/2015 |
| DE | 2744824 | A1 | 4/1978 |
| DE | 2903159 | A1 | 7/1980 |
| DE | 3114135 | A1 | 10/1982 |
| DE | 4213426 | A1 | 10/1992 |
| DE | 4300307 | A1 | 7/1994 |
| EP | 0041022 | A1 | 12/1981 |
| EP | 0136950 | A2 | 4/1985 |
| EP | 0140552 | A2 | 5/1985 |
| EP | 0156774 | A2 | 10/1985 |
| EP | 0213817 | A1 | 3/1987 |
| EP | 0216532 | A1 | 4/1987 |
| EP | 0220029 | A1 | 4/1987 |
| EP | 0273468 | A2 | 7/1988 |
| EP | 0324166 | A2 | 7/1989 |
| EP | 0324635 | A1 | 7/1989 |
| EP | 0324637 | A1 | 7/1989 |
| EP | 0324638 | A1 | 7/1989 |
| EP | 0365153 | A1 | 4/1990 |
| EP | 0369324 | A1 | 5/1990 |
| EP | 0373762 | A1 | 6/1990 |
| EP | 0380025 | A2 | 8/1990 |
| EP | 0399701 | A1 | 11/1990 |
| EP | 0449394 | A2 | 10/1991 |
| EP | 0484677 | A1 | 5/1992 |
| EP | 0489436 | A1 | 6/1992 |
| EP | 0503662 | A1 | 9/1992 |
| EP | 0514139 | A2 | 11/1992 |
| EP | 0536903 | A2 | 4/1993 |
| EP | 0537572 | A2 | 4/1993 |
| EP | 0539762 | A1 | 5/1993 |
| EP | 0545029 | A1 | 6/1993 |
| EP | 0552050 | A2 | 7/1993 |
| EP | 0552423 | A2 | 7/1993 |
| EP | 0579038 | A1 | 1/1994 |
| EP | 0589306 | A2 | 3/1994 |
| EP | 0591946 | A1 | 4/1994 |
| EP | 0592243 | A2 | 4/1994 |
| EP | 0593920 | A1 | 4/1994 |
| EP | 0598202 | A1 | 5/1994 |
| EP | 0598579 | A1 | 5/1994 |
| EP | 0600182 | A2 | 6/1994 |
| EP | 0621006 | A1 | 10/1994 |
| EP | 0621009 | A1 | 10/1994 |
| EP | 0656188 | A2 | 6/1995 |
| EP | 0666057 | A2 | 8/1995 |
| EP | 0705571 | A1 | 4/1996 |
| EP | 0760230 | A1 | 3/1997 |
| EP | 1952769 | A2 | 8/2008 |
| EP | 2090253 | A2 | 8/2009 |
| EP | 2090254 | A1 | 8/2009 |
| EP | 2583630 | A2 | 4/2013 |
| EP | 2586382 | A2 | 5/2013 |
| EP | 2907456 | A1 | 8/2015 |
| FR | 391239 | A | 10/1908 |
| FR | 2542188 | A1 | 9/1984 |
| FR | 2660851 | A1 | 10/1991 |
| FR | 2681775 | A1 | 4/1993 |
| GB | 1352554 | A | 5/1974 |
| GB | 1452185 | A | 10/1976 |
| GB | 1555455 | A | 11/1979 |
| GB | 2048685 | A | 12/1980 |
| GB | 2070499 | A | 9/1981 |
| GB | 2141066 | A | 12/1984 |
| GB | 2165559 | A | 4/1986 |
| JP | 51149985 | | 12/1976 |
| JP | 2001087272 | | 4/2001 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 2008302247 | | 7/1983 |
| WO | 8910094 | A1 | 11/1989 |
| WO | 9210976 | A1 | 7/1992 |
| WO | 9308754 | A1 | 5/1993 |
| WO | 9314706 | A1 | 8/1993 |
| WO | 2004032760 | A2 | 4/2004 |
| WO | 2009071070 | A2 | 6/2009 |
| WO | 2015191887 | A1 | 12/2015 |
| WO | 2016025132 | A1 | 2/2016 |

OTHER PUBLICATIONS

Examination Report for European Patent Application No. 22765609.7 mailed Jul. 3, 2025, 8 pages.

* cited by examiner

SMALL DIAMETER LINEAR SURGICAL STAPLING APPARATUS

CROSS-REFERENCE TO RELATED APPLICATIONS

This application is a continuation of U.S. patent application Ser. No. 18/109,484, filed Feb. 14, 2023, which is a continuation of U.S. patent application Ser. No. 17/407,623, filed on Aug. 20, 2021, now U.S. Pat. No. 11,576,671, the entire contents of each of which are incorporated by reference herein.

TECHNICAL FIELD

This disclosure relates to surgical stapling apparatus and, more particularly, to surgical stapling apparatus configured to rotate, articulate, and fire within small diameter (e.g., 8 mm) passages.

BACKGROUND

Fasteners have traditionally been used to replace suturing when joining various body structures. Surgical stapling apparatus employed to apply these fasteners are generally designed to simultaneously cut and seal tissue to reduce the time and risks involved with surgical procedures. Surgical stapling apparatus that clamp, cut and/or staple tissue are well known in the art. Such surgical stapling apparatus include end effectors having two elongated jaw members used to capture or clamp tissue. These end effectors can be provided in the form of an elongate loading unit removably attachable to a housing assembly via an adapter to enable drive components of the housing assembly to operate the end effector in vivo, for instance, laparoscopically. In particular, one of the two jaw members of the end effector usually carries a staple cartridge that houses a plurality of staples positioned in rows, while the other of the two jaw members has an anvil for forming the staples as the staples are driven from the staple cartridge. In linear surgical stapling apparatus, for example, a stapling operation is effectuated by a cam bar, a drive sled or other similar mechanism having a cam member that travels longitudinally through channels defined in the staple cartridge and acts upon staple pushers in the channels to sequentially eject linear rows of staples from the staple cartridge. A knife is movably positioned between the linear rows of staples such that when the surgical stapling apparatus is positioned about tissue and actuated, the tissue is joined and/or simultaneously or nearly simultaneously cut.

SUMMARY

Surgical stapling apparatus are challenging to design, particularly when such instruments are required to fit rotation, articulation, and firing within small diameter tubes that are as small as 8 mm for providing tight access and/or effectuating thin and/or vascular tissue stapling. When cartridge detection technology is required, adding the supplementary challenge of incorporating electronic chip technology within the limited space provided by the small diameter, design efforts become further complicated.

According to one aspect, a surgical stapling apparatus includes a housing assembly and an adapter assembly. The adapter assembly defines a longitudinal axis and is selectively attachable to the housing assembly. The adapter assembly includes an end effector and an articulation assembly. The articulation assembly includes an articulation drive screw, an articulation nut threadedly mounted to the articulation drive screw, an articulation yolk coupled to the articulation nut, and an articulation tube that is positioned to move in response to movement of the articulation nut. Movement of the articulation tube causes the end effector to articulate relative to the longitudinal axis.

In aspects, the articulation tube may define a slot therein that receives the articulation yolk. The articulation tube may support an articulation joint on a distal end portion thereof. The articulation joint may be coupled to one or more articulation links that are axially movable to articulate the end effector in response to axial movement of the articulation tube. The articulation links may include a proximal articulation link and a distal articulation link. The distal articulation link may have a proximal end portion that is coupled to the proximal articulation link. The distal articulation link may have a distal end portion that is pivotably coupled to an articulation pin of the end effector.

In aspects, the surgical stapling apparatus may further include a firing assembly including a drive beam assembly that is positioned to advance through the end effector. The firing assembly may further include a firing drive screw that is positioned within the articulation tube. The firing drive screw may be threadedly coupled to a firing nut. The firing nut may be coupled to a firing tube. The firing tube may be axially advanceable through the articulation tube in response to axial movement of the firing nut. The firing nut may be positioned to translate in response to rotation of the firing drive screw. A firing rod may be secured to a distal end portion of the firing tube. The firing rod may be coupled to the drive beam assembly and positioned to advance the drive beam assembly through the end effector when the firing tube translates the firing rod distally.

In aspects, the surgical stapling apparatus may further include a rotation assembly having a driver that couples to a pinion. The pinion may be coupled to an annulus. The annulus may be coupled to a housing on a proximal end portion of the adapter assembly. The housing may be coupled to an outer tube. The outer tube may be coupled to the end effector, wherein rotation of the driver causes the end effector to rotate about the longitudinal axis.

According to one aspect, this disclosure is directed to a surgical stapling apparatus including a housing assembly, an elongated shaft assembly, an anvil assembly, a cartridge assembly, and an articulation assembly. The elongated shaft assembly defines a longitudinal axis and has a distal end portion and a proximal end portion. The proximal end portion is selectively attachable to the housing assembly. The anvil assembly is supported on the distal end portion of the elongated shaft assembly. The cartridge assembly is selectively attachable to the anvil assembly to secure the cartridge assembly to the elongated shaft assembly. The articulation assembly includes an articulation drive screw, an articulation nut threadedly mounted to the articulation drive screw, an articulation yolk coupled to the articulation nut, and an articulation tube that is positioned to move in response to movement of the articulation nut, wherein movement of the articulation tube causes the anvil and cartridge assemblies to articulate relative to the longitudinal axis.

In aspects, the anvil assembly may include an anvil and tissue stops on a proximal end portion thereof. The tissue stops may define cartridge tab slots therethrough, and wherein the cartridge assembly may include proximal tabs that are receivable within the cartridge tab slots of the anvil assembly to couple the cartridge assembly to the anvil assembly. The cartridge assembly may include a cartridge and a support plate. The proximal tabs may extend from the support plate.

In aspects, the articulation tube may define a slot therein that receives the articulation yolk. The articulation tube may support an articulation joint on a distal end portion thereof. The articulation joint may be coupled to one or more articulation links that are movable to articulate the anvil and cartridge assemblies in response to movement of the articulation tube. The one or more articulation links may include a proximal articulation link and a distal articulation link. The distal articulation link may have a proximal end portion that is coupled to the proximal articulation link. The distal articulation link may have a distal end portion that is pivotably coupled to an articulation pin of the anvil assembly.

According to yet another aspect, this disclosure is directed to an adapter assembly of a surgical stapling apparatus. The adapter assembly includes a proximal housing, an articulation assembly, an elongated shaft assembly, and an end effector. The articulation assembly is supported by the proximal housing. The articulation assembly includes an articulation drive screw, an articulation nut threadedly mounted to the articulation drive screw, an articulation yolk coupled to the articulation nut, and an articulation tube positioned to move in response to movement of the articulation nut. The elongated shaft assembly is coupled to the proximal housing and defines a longitudinal axis. The elongated shaft assembly has a proximal end portion and a distal end portion. The end effector is supported on the distal end portion of the elongated shaft assembly and includes an anvil assembly and a cartridge assembly selectively attachable to the anvil assembly. Rotation of the articulation drive screw causes the end effector to articulate relative to the longitudinal axis.

In aspects, the adapter assembly may further include a firing assembly. The firing assembly may include a drive beam assembly that is positioned to advance through the cartridge assembly. The firing assembly may further include a firing drive screw that is positioned within the articulation tube. The firing drive screw may be threadedly coupled to a firing nut. The firing nut may be coupled to a firing tube. The firing tube may be being axially advanceable through the articulation tube in response to axial movement of the firing nut. The firing nut may be positioned to translate in response to rotation of the firing drive screw.

In aspects, a firing rod may be secured to a distal end portion of the firing tube. The firing rod may be coupled to the drive beam assembly and positioned to advance the drive beam assembly through the end effector when the firing tube translates the firing rod distally.

Other aspects, features, and advantages will be apparent from the description, the drawings, and the claims that follow.

BRIEF DESCRIPTION OF DRAWINGS

The accompanying drawings, which are incorporated in and constitute a part of this specification, illustrate aspects of the disclosure and, together with a general description of the disclosure given above and the detailed description given below, explain the principles of this disclosure, wherein.

DETAILED DESCRIPTION

Figure 1:
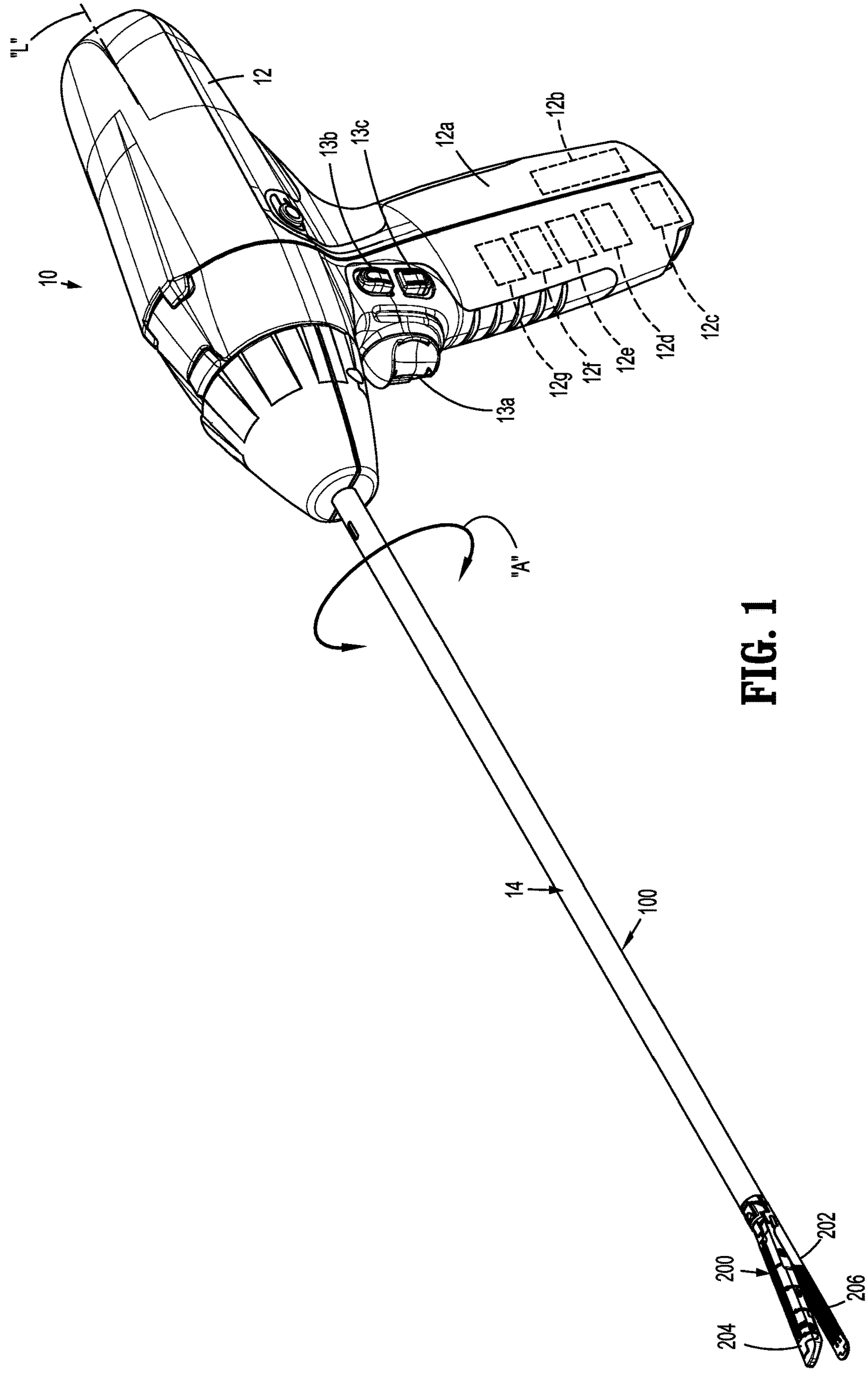
FIG. 1 is a perspective view of an exemplary surgical stapling apparatus in accordance with the principles of this disclosure.
Figure 2:
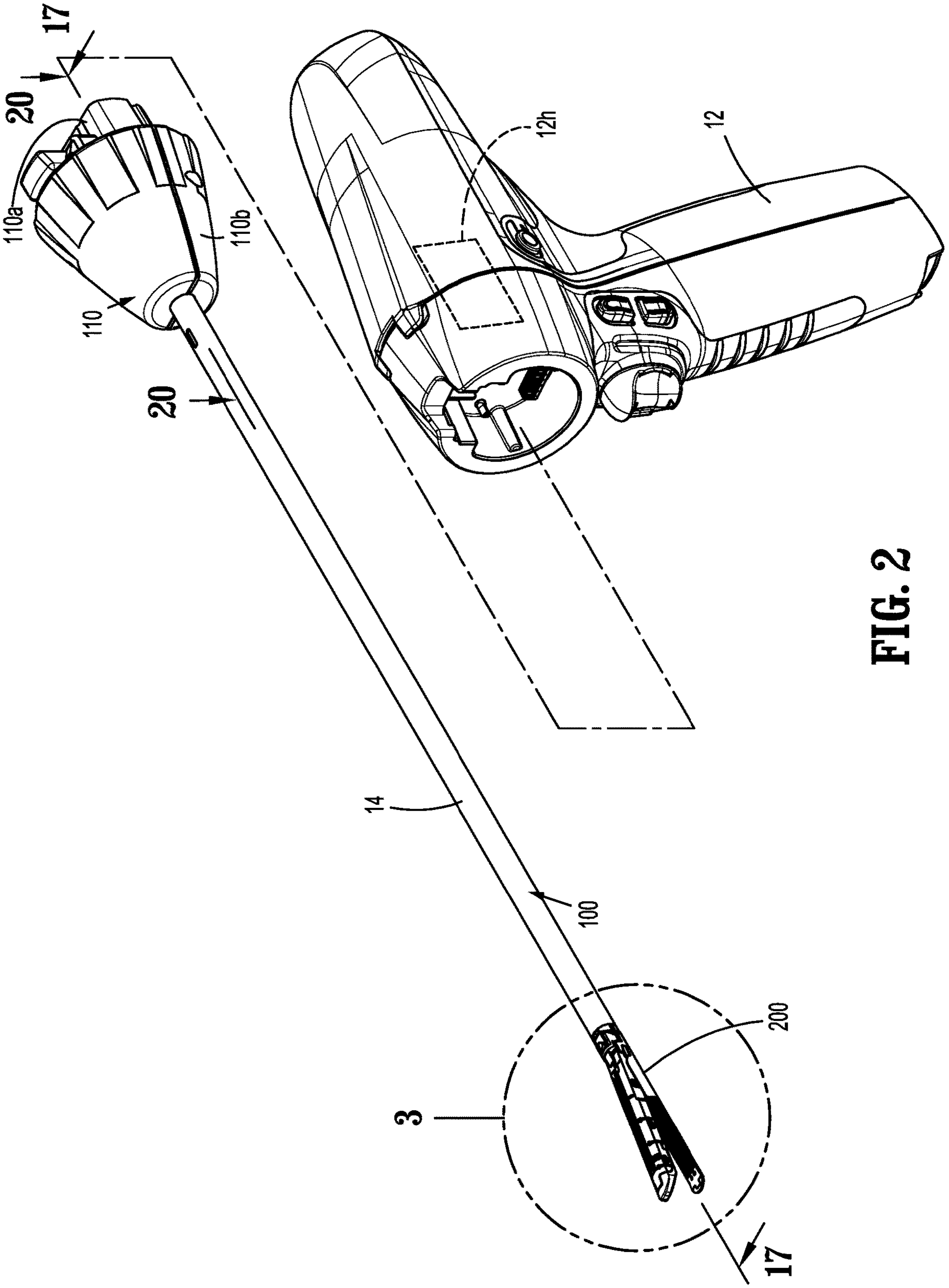
FIG. 2 is a perspective view of the surgical stapling apparatus of FIG. 1 with an elongated shaft assembly of the surgical stapling apparatus shown separate from a housing assembly of the surgical stapling apparatus, the elongated shaft assembly including an end effector supported on a distal end portion thereof.
Figure 3:
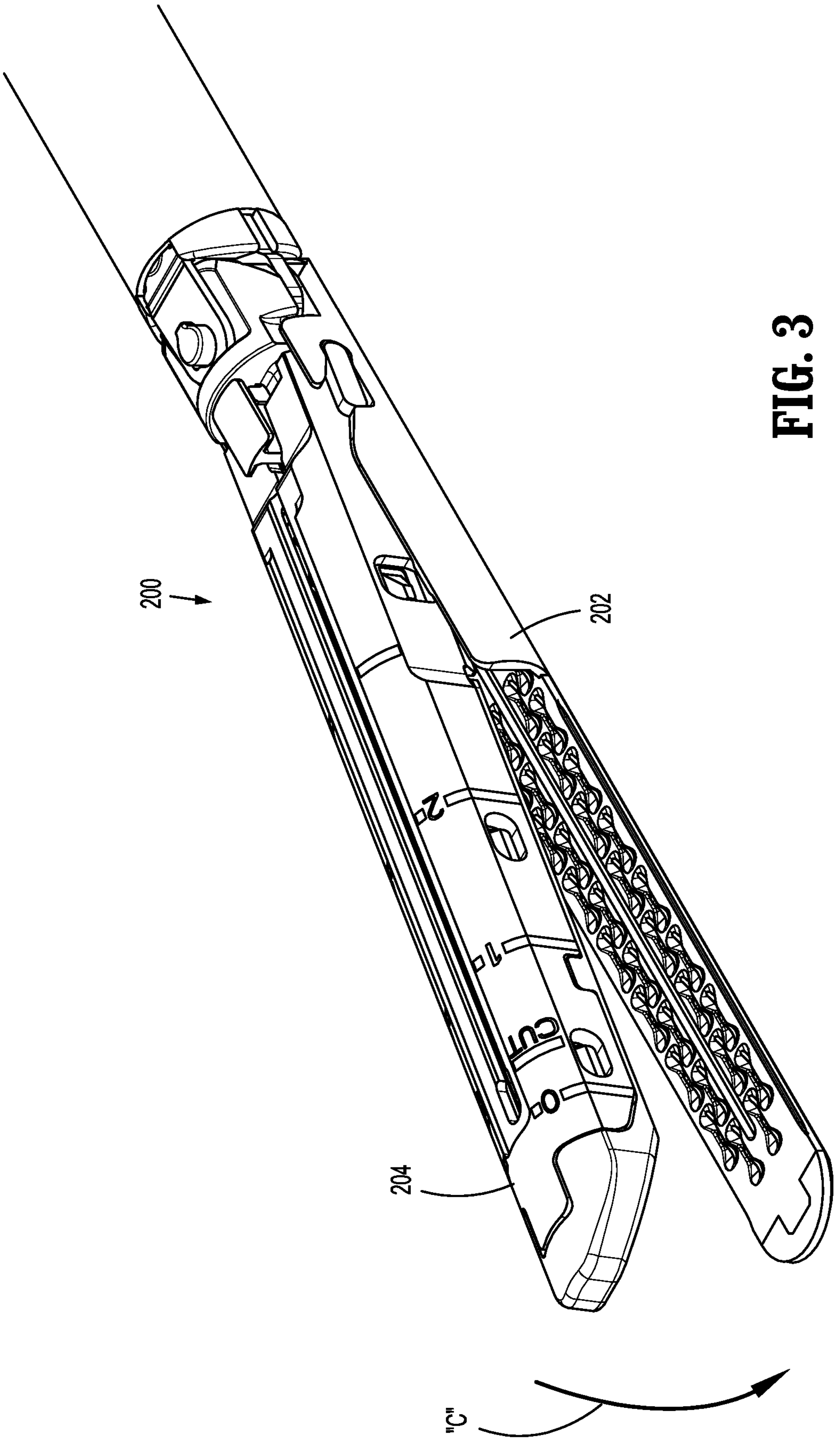
FIG. 3 is an enlarged view of the indicated area of detail shown in FIG. 2, the view illustrating the end effector.
Figure 4:
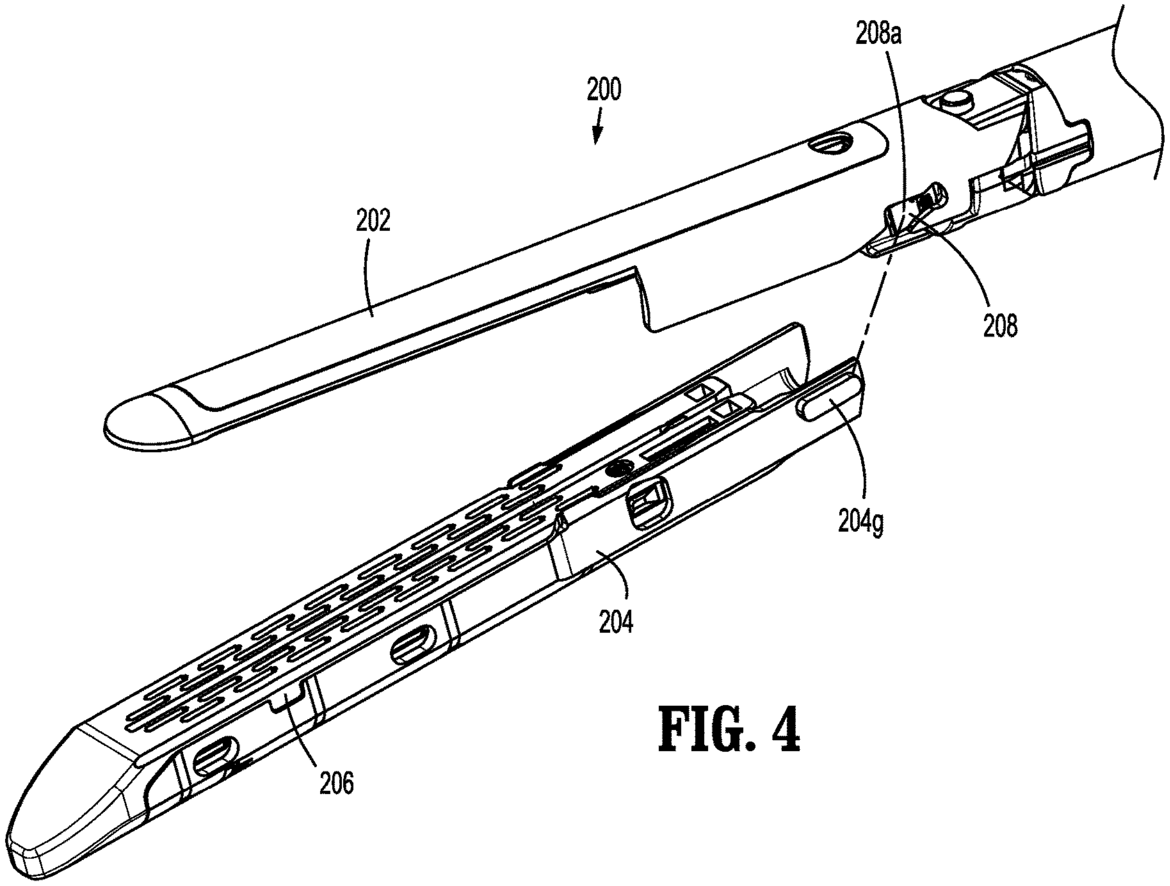
FIG. 4 is a perspective view illustrating a cartridge assembly of the end effector of FIG. 3 separated from an anvil assembly of the end effector of FIG. 3.
Figure 5:
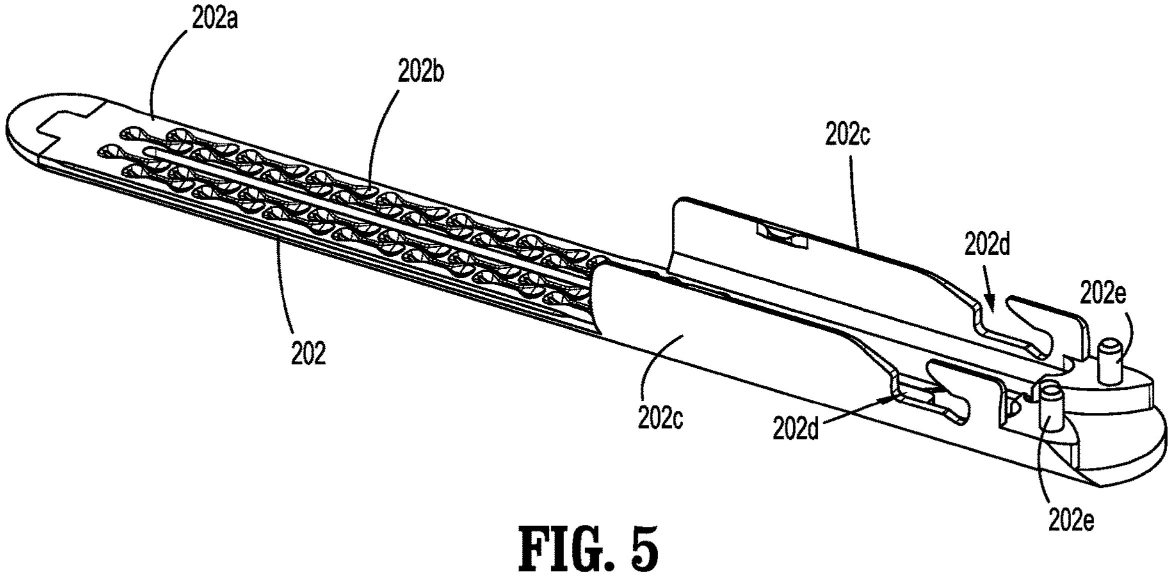
FIG. 5 is a perspective view of the anvil assembly of FIG. 4.
Figure 7:
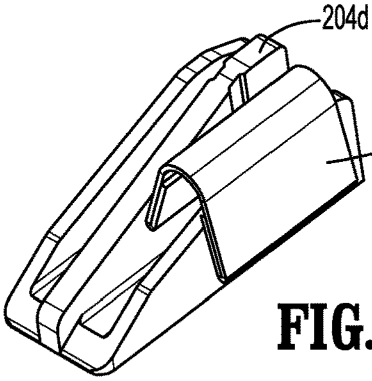
FIG. 7 is an enlarged view of a sled and a lockout spring of the cartridge assembly of FIG. 6.
Figure 6:
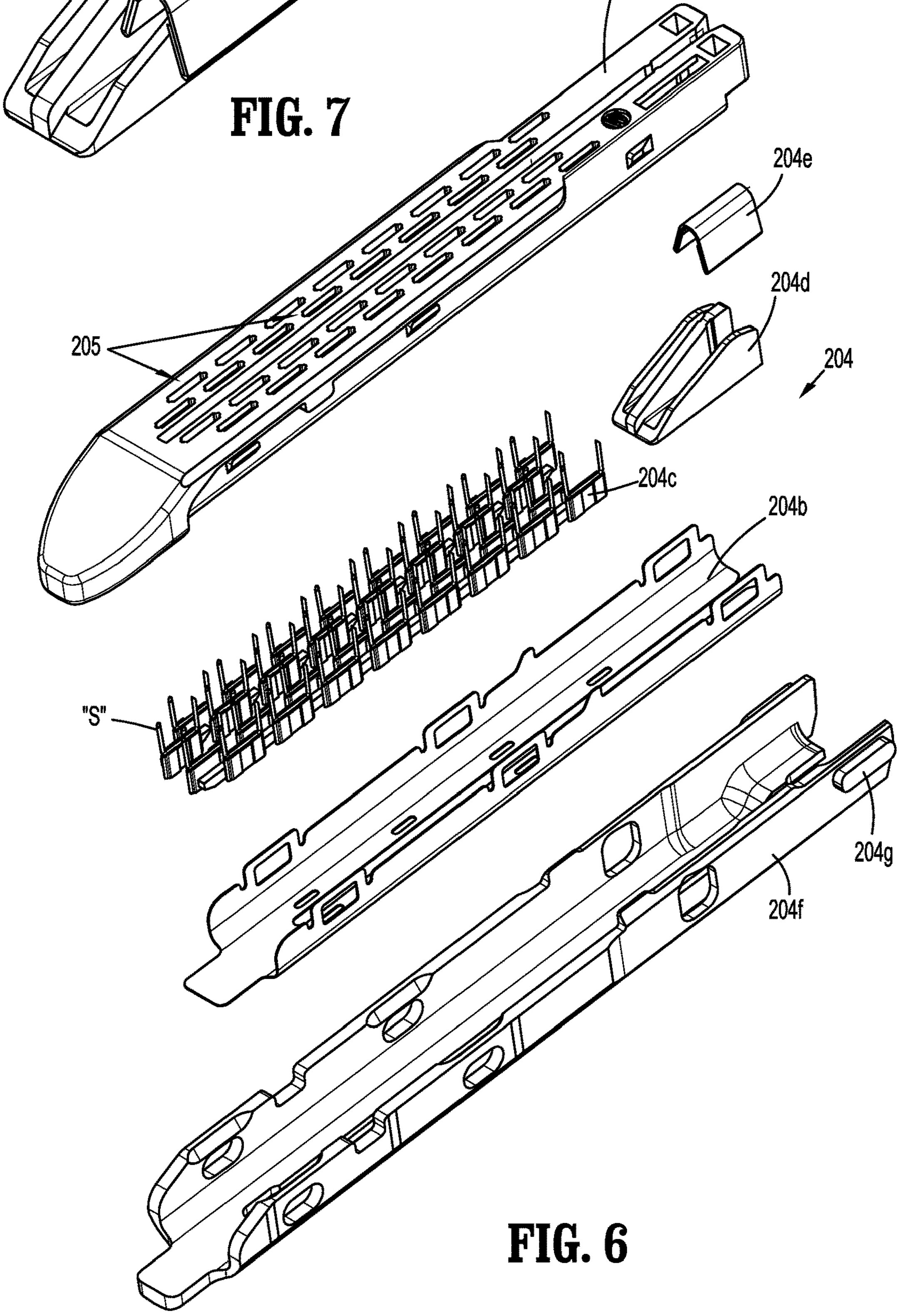
FIG. 6 is a perspective view, with parts separated, of the cartridge assembly of FIG. 4.

Aspects of the disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

Further, although the surgical instrument described herein is provided in connection with a powered laparoscopic surgical stapling apparatus for brevity, the disclosed surgical instrument can include any powered, manual, or robotically-controlled surgical instruments such as a clip applier, stitching device, energy-based device (e.g., a bipolar or monopolar forceps) or the like, and/or other surgical stapling apparatus such as a circular stapler, a transverse stapler, or an open stapler. For a detailed description of the structure and function of exemplary surgical stapling apparatus, one or more components of which may be included, or modified for use with the disclosed aspects, reference may be made to U.S. Pat. Nos. 9,713,470; 8,806,973; 8,256,656; 8,157,152; 8,070,033 7,819,896; 7,770,774; 7,334,717; 7,128,253; 5,964,394; and 5,915,616, the entire contents of each of which are incorporated herein by reference.

Turning now to FIGS. 1-28, this disclosure is directed to a surgical stapling apparatus 10. With reference to FIGS. 1-7, surgical stapling apparatus 10 includes a housing assembly 12 (which may include one or more handles that may be manually actuatable to fire surgical stapling apparatus 10) and an elongated shaft assembly 14 that is removably secured to housing assembly 12. Elongated shaft assembly 14 extends distally from housing assembly 12 and defines a longitudinal axis "L" therealong. Elongated shaft assembly 14 includes an adapter assembly 100 having a proximal end portion removably secured to housing assembly 12. Adapter assembly 100 extends distally from housing assembly 12 to an end effector 200. End effector 200 includes an anvil assembly 202 and a cartridge assembly 204 that houses a plurality of fasteners (e.g., staples "S") (FIG. 6) in a reload or cartridge 206 thereof that may be reusable and/or disposable and selectively replaceable.

Anvil assembly 202 of end effector 200 includes an anvil 202*a* defining tissue pockets 202*b* against which the plurality of staples "S" is formed upon a firing of surgical stapling apparatus 10. Anvil assembly 202 further includes tissue stops 202*c* on a proximal end portion thereof. The tissue stops 202*c* define cartridge tab slots 202*d* therethrough configured to secure cartridge assembly 204 to anvil assembly 202. Anvil assembly 202 further includes articulation posts 202*e* on a proximal end portion thereof for facilitating pivotal (articulating) movement of end effector 200 relative to longitudinal axis "L."

Cartridge assembly 204 of end effector 200 includes an upper cartridge body 204*a* and a lower cartridge body 204*b* that support fasteners, pushers 204*c*, and a sled 204*d* therebetween. Upper cartridge body 204*a* defines a plurality of staple slots 205 that supports fasteners therein. A spring lock 204*e* is supported on sled 204*d* and positioned to spring open from an unlocked position (FIG. 27) to a locked position (FIG. 28) when sled 204*d* advances distally through cartridge assembly 204 to prevent cartridge assembly 204 from being refired. Cartridge assembly 204 further includes a support plate 204*f* that couples to upper and lower cartridge bodies 204*a*, 204*b*. Support plate 204*f* includes proximal tabs 204*g* on opposite sides thereof that are received within cartridge tab slots 202*d* of anvil assembly 202 to secure cartridge assembly 204 to anvil assembly 202.

End effector 200 further includes a sensor assembly 208 supported by anvil assembly 202. Sensor assembly 208 may include a cartridge ID sensor or cartridge detector 208*a* disposed in electrical communication with housing assembly 12 (e.g., a controller thereof). The cartridge detector 208*a* is disposed in registration with cartridge tab slots 202*d* such that cartridge detector 208*a* is configured to detect when proximal tabs 204*g* of cartridge assembly 204 are received within cartridge tab slots 202*d* of anvil assembly 202 and communicate a signal to a controller 208*c* of sensory assembly 208 via a flex cable 208*d* extending through elongated shaft assembly 14 (see FIGS. 14-16). The signal indicative of the securement of the cartridge assembly 204 to the anvil assembly 202. The controller 208*c* disposed within a proximal end portion of elongated shaft assembly 14. Flex cable 208*d* includes a distal linear undulation 208*e* and a proximal rotational coil 208*f* that are coupled together, and to controller 208*c* and cartridge detector 208*a*, via various cable segments 208*g*. Controller 208*c* is configured to electrically communicate with housing assembly 12 (e.g., with a controller 12*c* supported within housing assembly 12).

Housing assembly 12 of surgical stapling apparatus 10 includes a housing 12*a* configured for selective removable receipt of a rechargeable battery 12*b*. Battery 12*b* is configured to supply power to electrical components of surgical stapling apparatus 10. Housing 12*a* supports controller 12*c* (e.g., a circuit board) therein. Controller 12*c* is configured to control various operations of surgical stapling apparatus 10 and includes any number of electronic components such as a memory 12*d*, a processor 12*e*, a network interface 12*f*, and/or other input/output modules 12*g*. Controller 12*c* may be coupled to a local or remote display device (not shown) for outputting information and/or data such as a condition of components of surgical stapling apparatus 10 and/or tissue grasped by end effector 200.

Surgical stapling apparatus 10 further includes a drive mechanism 12*h* configured to drive mechanical and/or electrical components such as rotatable shafts and/or gear components (not shown) within housing 12*a* in order to perform various operations of surgical stapling apparatus 10. For instance, drive mechanism 12*h* may be operable to selectively rotate and/or articulate end effector 200 about, and/or relative to, the longitudinal axis "L" of surgical stapling apparatus 10, as indicated by arrows "A" (FIG. 1) and "B" (FIGS. 23 and 24), respectively; to selectively move cartridge assembly 204 relative to the anvil assembly 202 and/or vice versa, as indicated by arrow "C" to selectively clamp tissue; and/or to fire surgical stapling apparatus 10 for fastening and/or cutting the clamped tissue. Battery 12*b*, controller 12*c*, and/or drive mechanism 12*h* may be operably coupled to one or more actuators 13*a*, 13*b*, and 13*c* such as finger-actuated control buttons, rocker devices, and/or the like to effectuate various functions of surgical stapling apparatus 10 such as those described above.

As best seen in FIGS. 8-28, adapter assembly 100 of elongated shaft assembly 14 includes an outer housing 110 on a proximal end portion thereof and an outer tube 109 that extends distally from outer housing 110 to a support assembly 108. Support assembly 108 includes an upper shell 108*a* and a lower shell 108*b* that couple together to support a drive beam assembly 150 therein. The support assembly 108 has a distal end portion pivotably coupled to a proximal end of end effector 200 to enable end effector 200 to articulate relative to longitudinal axis "L." Outer housing 110 supports a drive assembly 112 therein. Outer housing 110 has a proximal outer housing 110*a* and a distal outer housing 110*b* that extends distally from proximal outer housing 110*a*. Proximal outer housing 110*a* supports an electrical assembly 110*c* and a plurality of drive couplers 110*d* that electromechanically couple to drive mechanism 12*h* of housing assembly 12 for effecting rotation, articulation, and firing of surgical stapling apparatus 10. Electrical assembly 110*c* is configured to electrically communicate with, for example, controller 12*c* of housing assembly 12 when adapter 100 is coupled to housing assembly 12 and when drive couplers 110*d* mechanically engage drive mechanism 12*h*, which may include, for instance, a plurality of rotatable actuators (shown) to impart mechanical force (e.g., rotational force) through drive assembly 112 of adapter assembly 100. Specifically, a first actuator 110*z* is configured to facilitate articulation of end effector 200 relative to longitudinal axis "L," a second actuator 110*y* is configured to fire the surgical stapling apparatus 10 for clamping, cutting, and fastening tissue, and a third actuator 110*x* is configured to rotate adapter assembly 100 (and thus end effector 200) about longitudinal axis "L" and relative to housing assembly 12. Actuators 110*z*, 110*y*, 110*x* are spring biased by springs 121 relative adapter assembly 100. Distal outer housing 110*b* includes an upper housing 110*e* and a lower housing 110*f* that define tab recesses 110*g* therein.

A proximal end portion of adapter assembly 100 further includes an inner body assembly 111 and an actuator mount 113 coupled to inner body assembly 111. The inner body assembly 111 and the actuator mount 113 are supported within outer housing 110.

Adapter assembly 100 of elongated shaft assembly 14 includes an articulation assembly 120 configured to articulate end effector 200 relative to longitudinal axis "L," a firing assembly 140 configured to fire end effector 200 (e.g., to clamp, fasten, and cut tissue), and a rotation assembly 160 configured to rotate end effector 200 about longitudinal axis "L."

Figure 8:
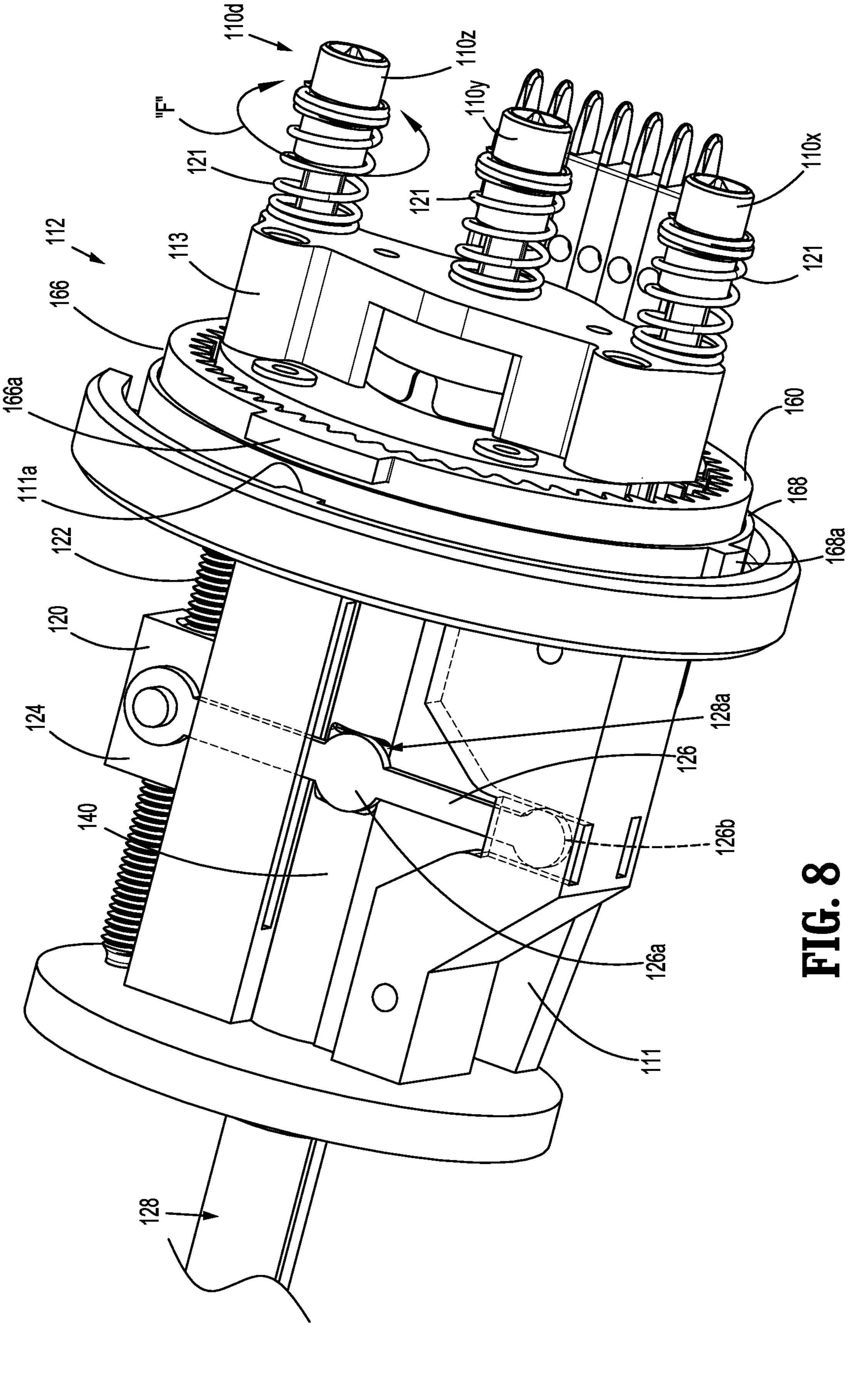
FIG. 8 is an enlarged perspective view of a proximal end portion of the elongated shaft assembly with portions removed for clarity.
Figure 9:
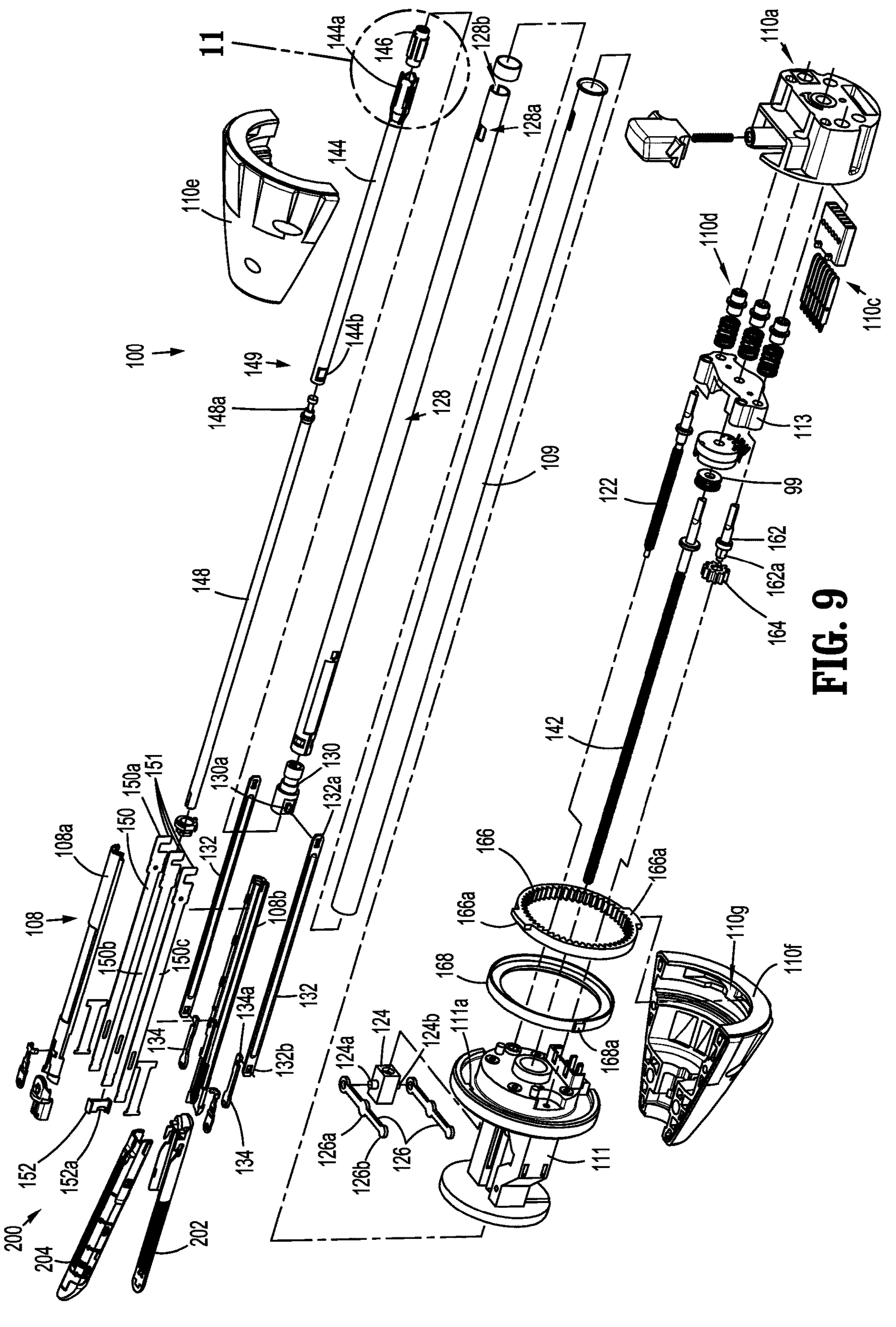
FIG. 9 is a perspective view, with parts separated, of the elongated shaft assembly.
Figure 11:
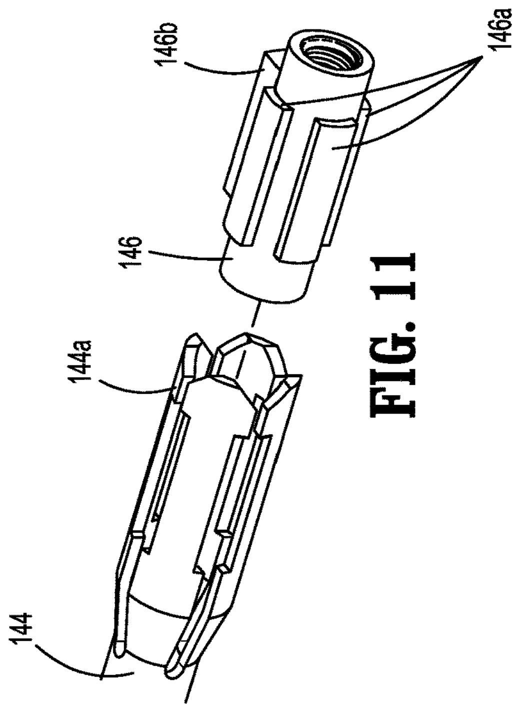
FIG. 11 is an enlarged perspective view of the indicated area of detail shown in FIG. 9.
Figure 10:
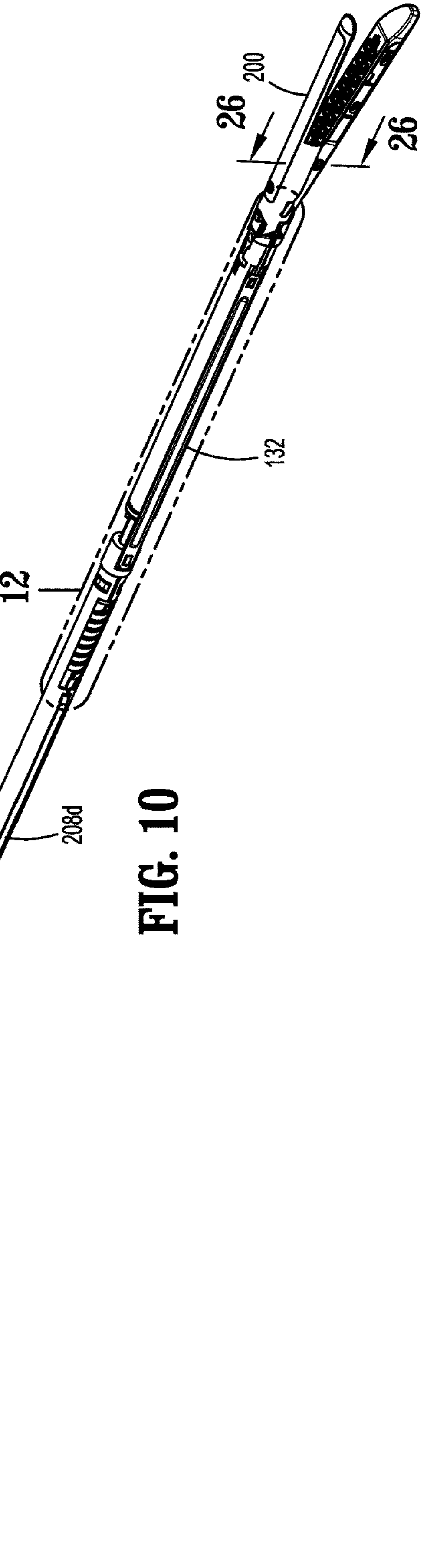
FIG. 10 is a perspective view of the elongated shaft assembly with portions thereof removed for clarity.
Figure 12:
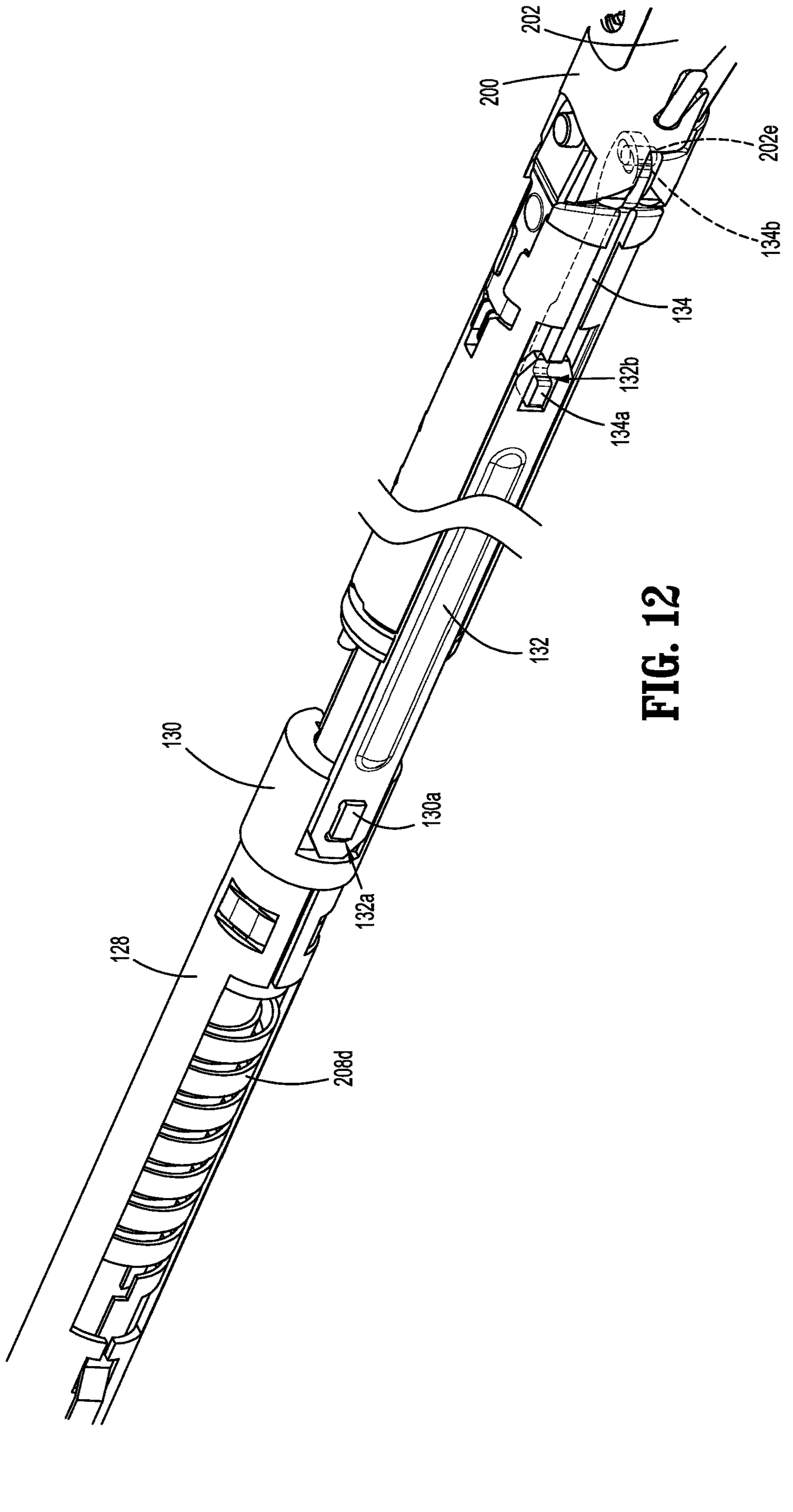
FIG. 12 is an enlarged perspective view of the indicated area of detail shown in FIG. 10.
Figure 13:
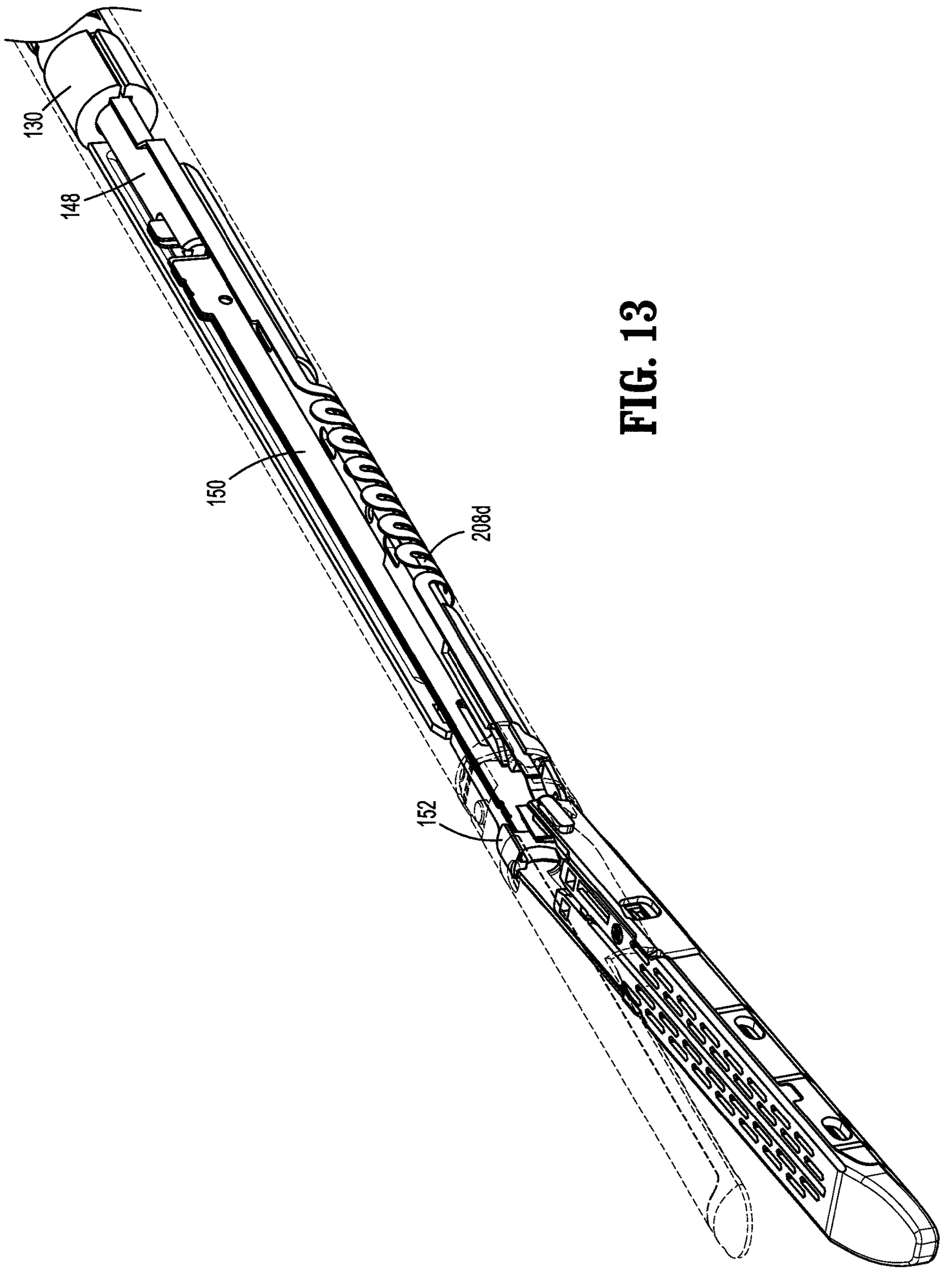
FIG. 13 is a perspective view of a distal portion of the elongated shaft assembly with portions thereof shown in phantom for clarity.
Figures 14, 15, 16:
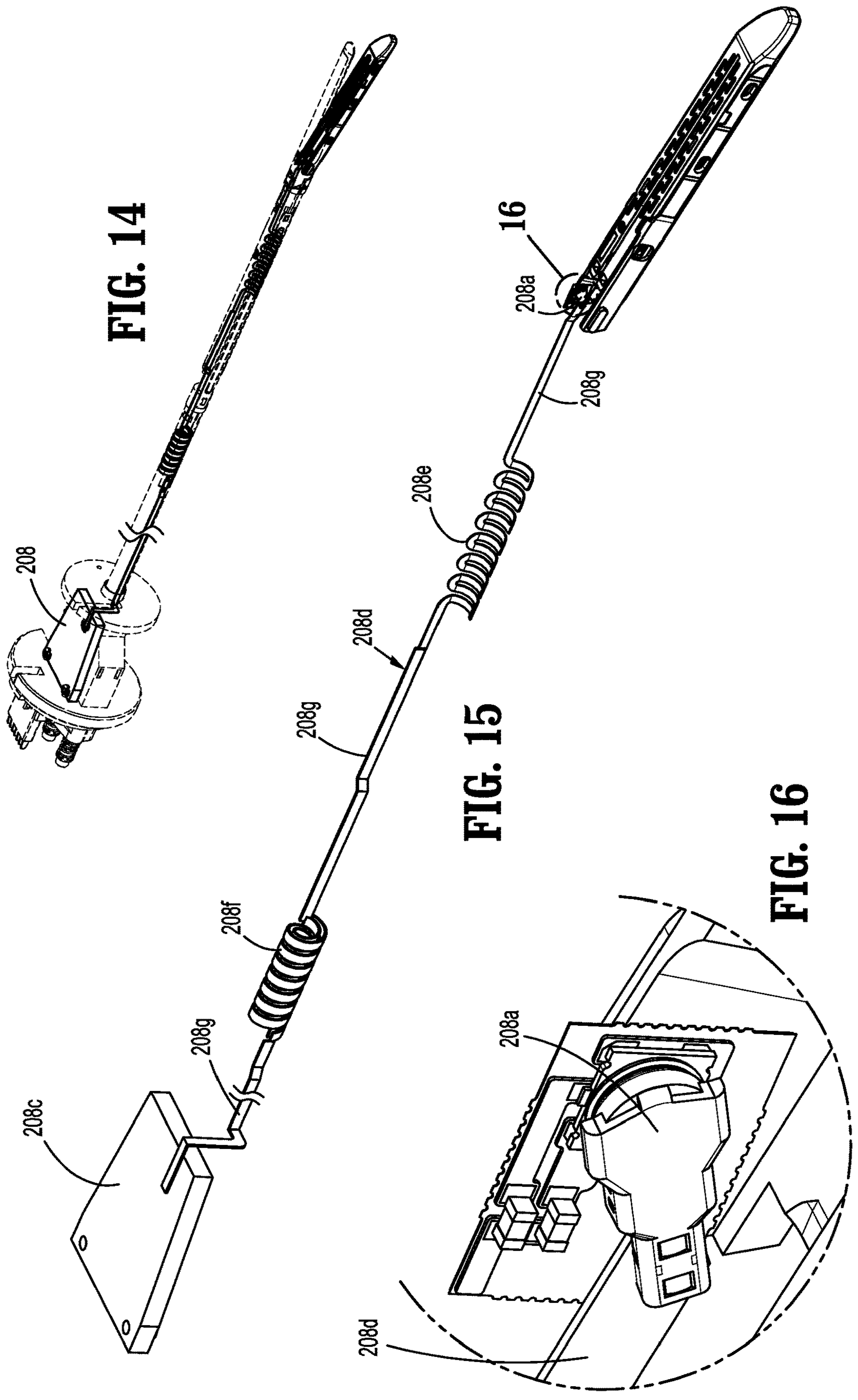
FIGS. 14 and 15 are perspective views of the elongated shaft assembly with portions thereof removed or shown in phantom for clarity.
FIG. 16 is an enlarged view of the indicated area of detail shown in FIG. 15.
Figure 17:
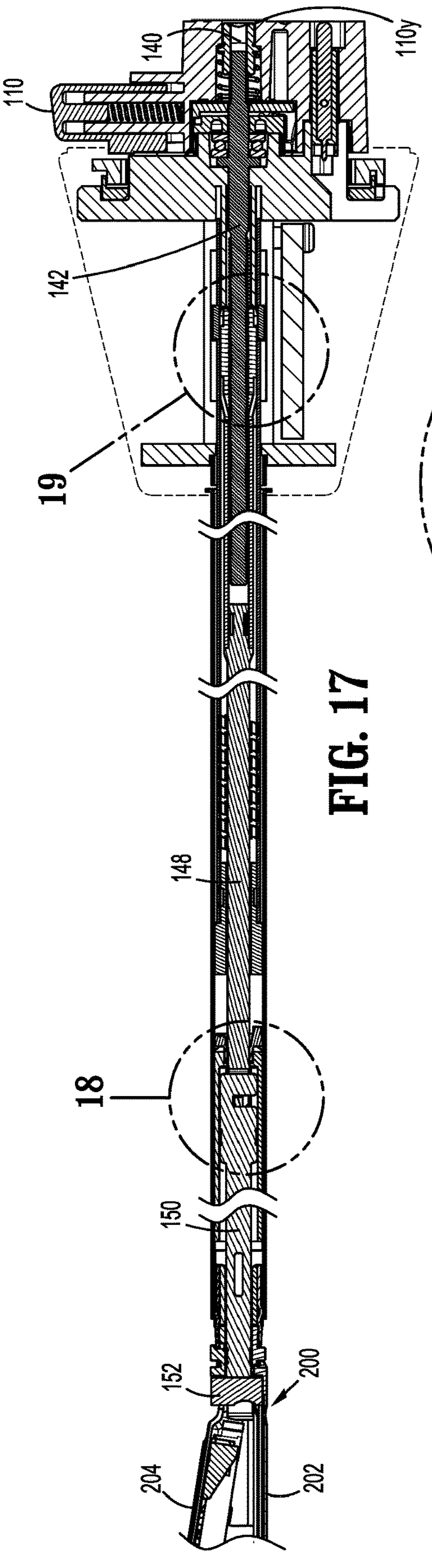
FIG. 17 is a cross-sectional view of the elongated shaft assembly as taken along section line 17-17 shown in FIG. 2.
Figure 19:
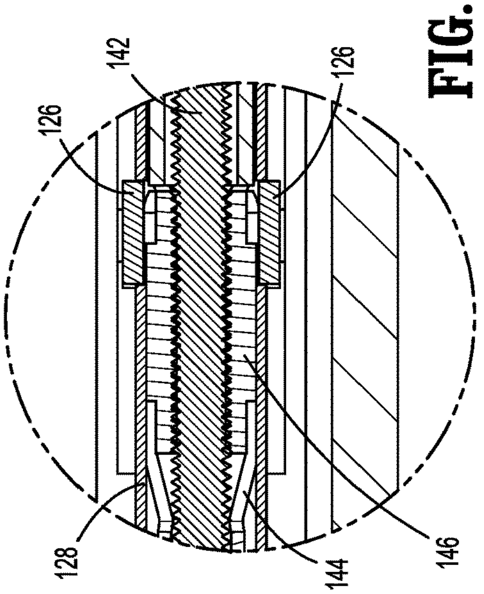
FIGS. 18 and 19 are enlarged views of the indicated areas of detail shown in FIG. 17.
Figure 18:
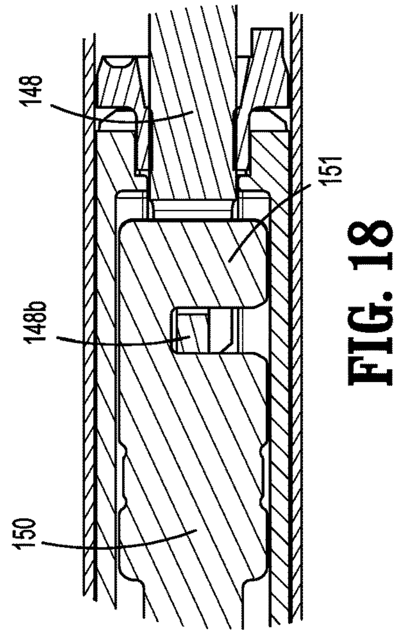
Figure 20:
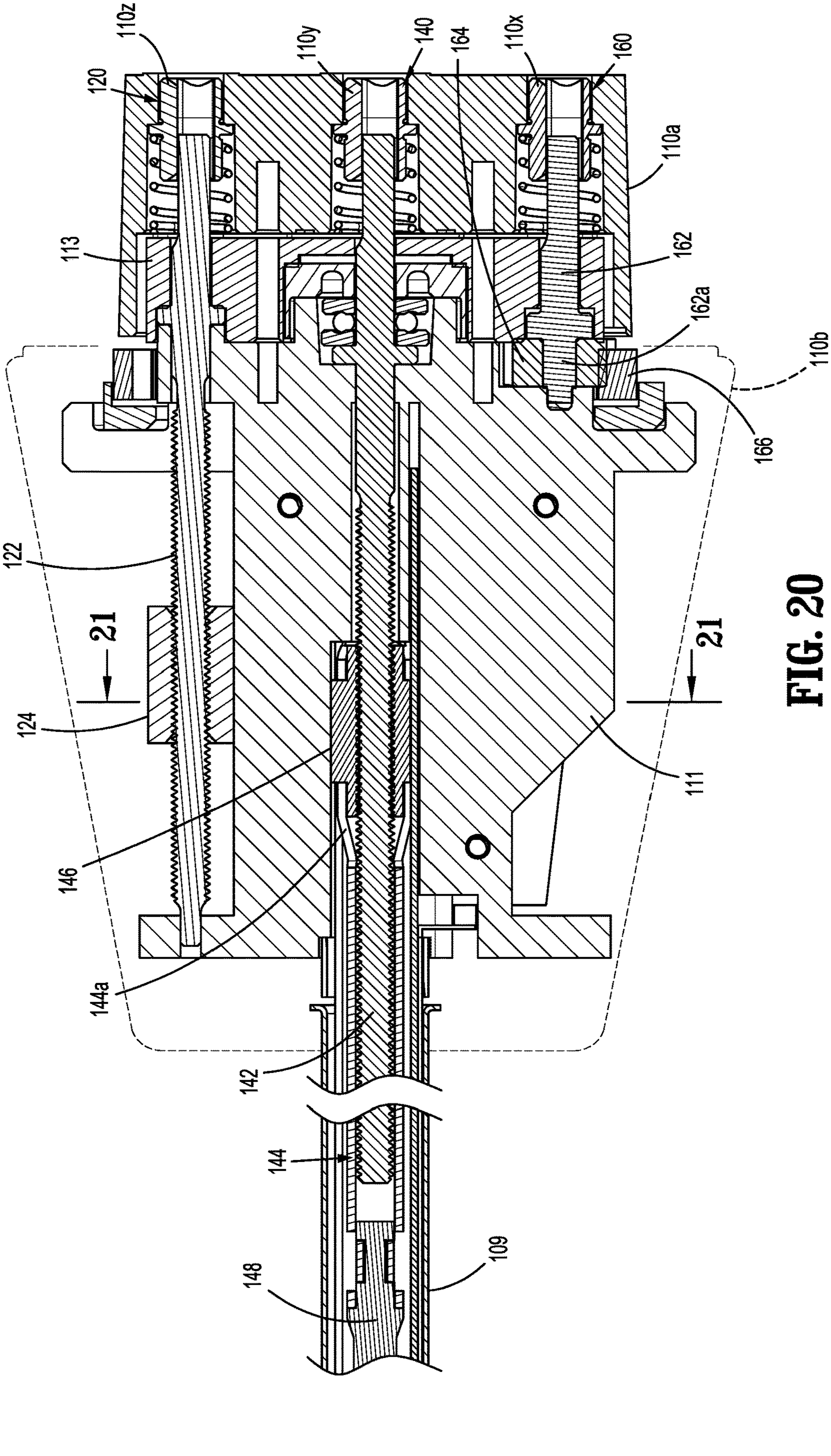
FIG. 20 is a cross-sectional view of the elongated shaft assembly as taken along section line 20-20 shown in FIG. 2.
Figure 21:
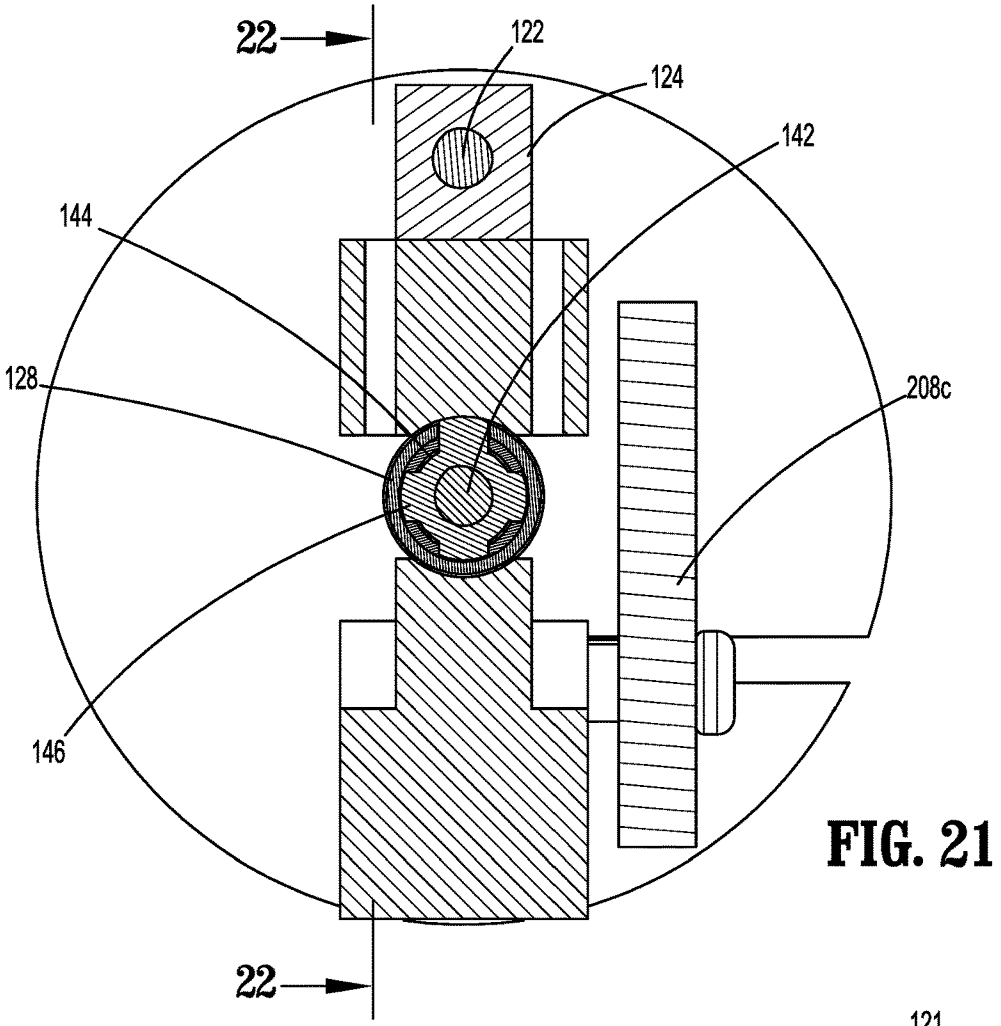
FIG. 21 is a cross-sectional view as taken along section line 21-21 shown in FIG. 20.
Figure 22:
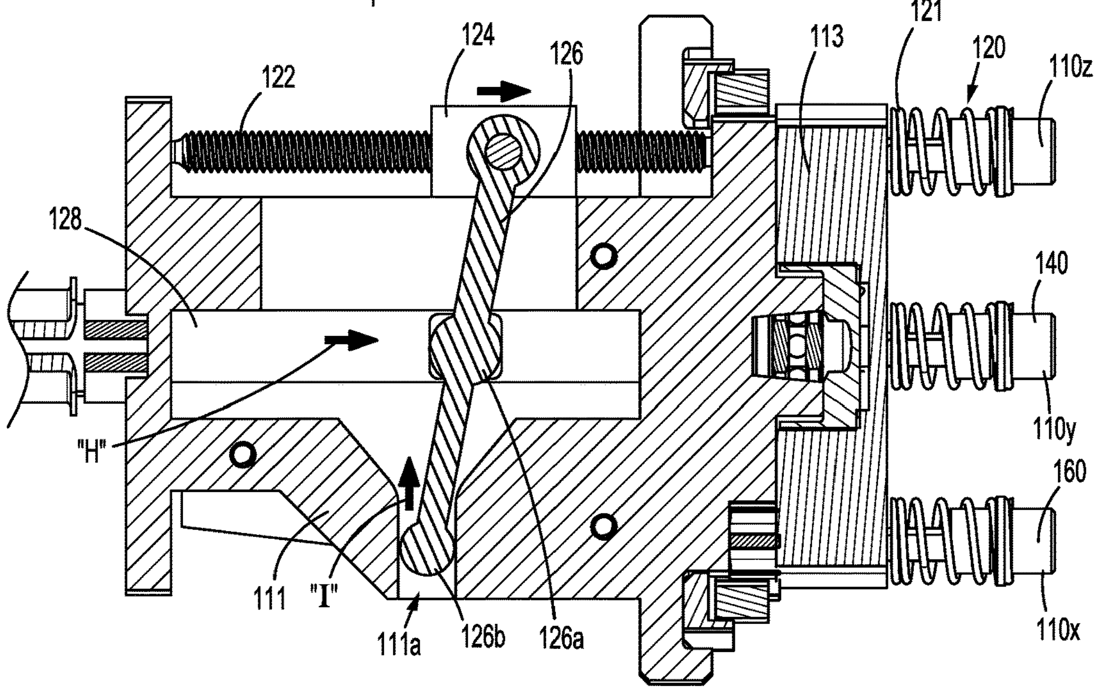
FIG. 22 is a cross-sectional view as taken along section line 22-22 shown in FIG. 21.
Figure 23:
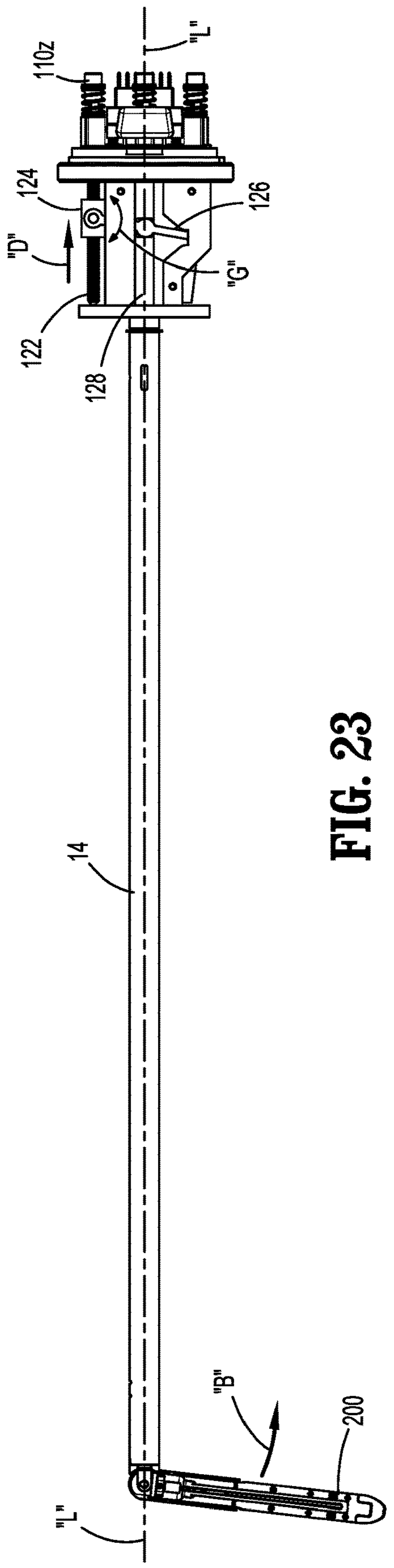
FIGS. 23 and 24 are progressive views illustrating articulation of the end effector relative to a longitudinal axis of the elongated shaft assembly.
Figure 24:
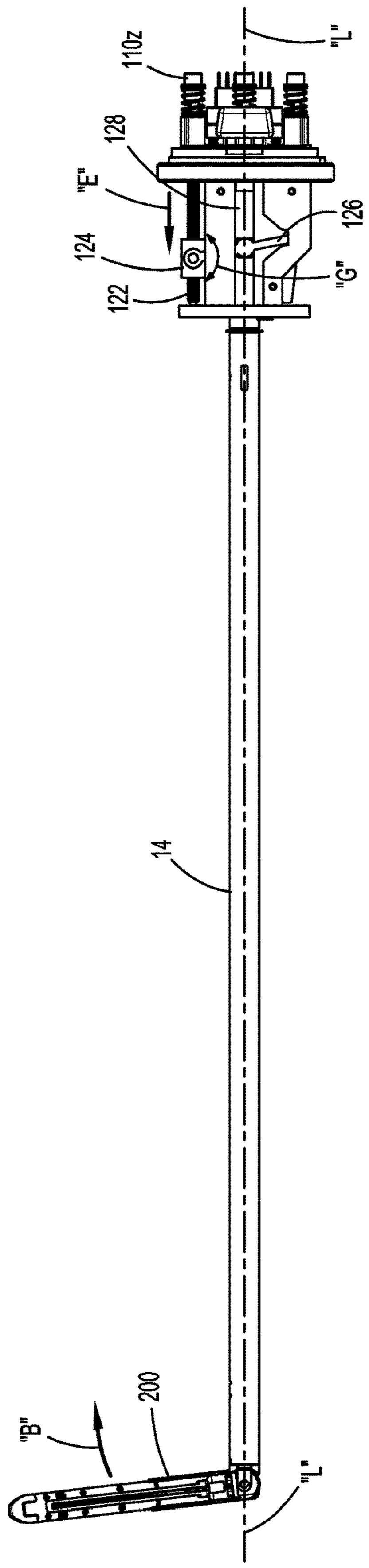

Articulation assembly 120 of adapter assembly 100 includes first actuator 110*z* on a proximal end portion thereof that mechanically engages with drive mechanism 12*h* of housing assembly 12. Articulation assembly 120 also includes an articulation drive screw 122 that is mechanically coupled to first actuator 110*z*. Articulation drive screw 122 extends distally from first actuator 110*z* and through actuator mount 113. Articulation assembly 120 further includes an articulation nut 124 threadedly coupled to articulation drive screw 122 and axially advanceable therealong. Articulation nut 124 is configured to translate in proximal and/or distal directions, as indicated by arrows "D" and "E" (FIGS. 23 and 24), respectively, in response to rotation of articulation drive screw 122, as indicted by arrows "F" (FIG. 8). Articulation assembly 120 further includes a pair of articulation yolks 126 pinned to articulation nut 124 via pins 124*a*, 124*b* extending from articulation nut 124. Pins 124*a*, 124*b* enable articulation yolks 126 to pivot about pins 124*a*, 124*b*, as indicated by arrows "G" (FIGS. 23 and 24), when articulation nut 124 axially translates along articulation drive screw 122. Articulation yolks 126 include a drive plate 126*a* and an end plate 126*b*. Articulation assembly 120 also includes an articulation tube 128 supported within outer tube 109 and coupled to articulation yolks 126 via drive plates 126*a*. Drive plates 126*a* of articulation yolks 126 are received within drive notches 128*a* defined within a proximal end portion of articulation tube 128. End plates 126*b* of articulation yolks 126 are slidably (vertically as indicated by arrows "I" in FIG. 22) and rotatably received within a tapered guide channel 111*a* defined within inner body assembly 111. Drive plates 126*a* are configured to cause articulation tube 128 to axially translate, as indicated by arrows "H" (FIG. 22), as articulation yolks 126 pivot about articulation nut 124.

Articulation assembly 120 of adapter assembly 100 further includes an articulation joint 130 coupled to a distal end portion of articulation tube 128, proximal articulation links 132 that have proximal notches 132*a* coupled to distal tabs 130*a* on opposed sides of articulation joint 130, and distal articulation links 134 that are coupled to distal notches 132*b* of proximal articulation links 132. Distal articulation links 134 include proximal hooks 134*a* received within distal notches 132*b* of proximal articulation links 132 and distal apertures 134*b* (FIG. 12) defined therethrough that receive articulation posts 202*e* of anvil assembly 202 (see FIG. 5). Articulation joint 130 is positioned to provide a wire path channel therethrough for flex cable 208*d*.

Figure 25:
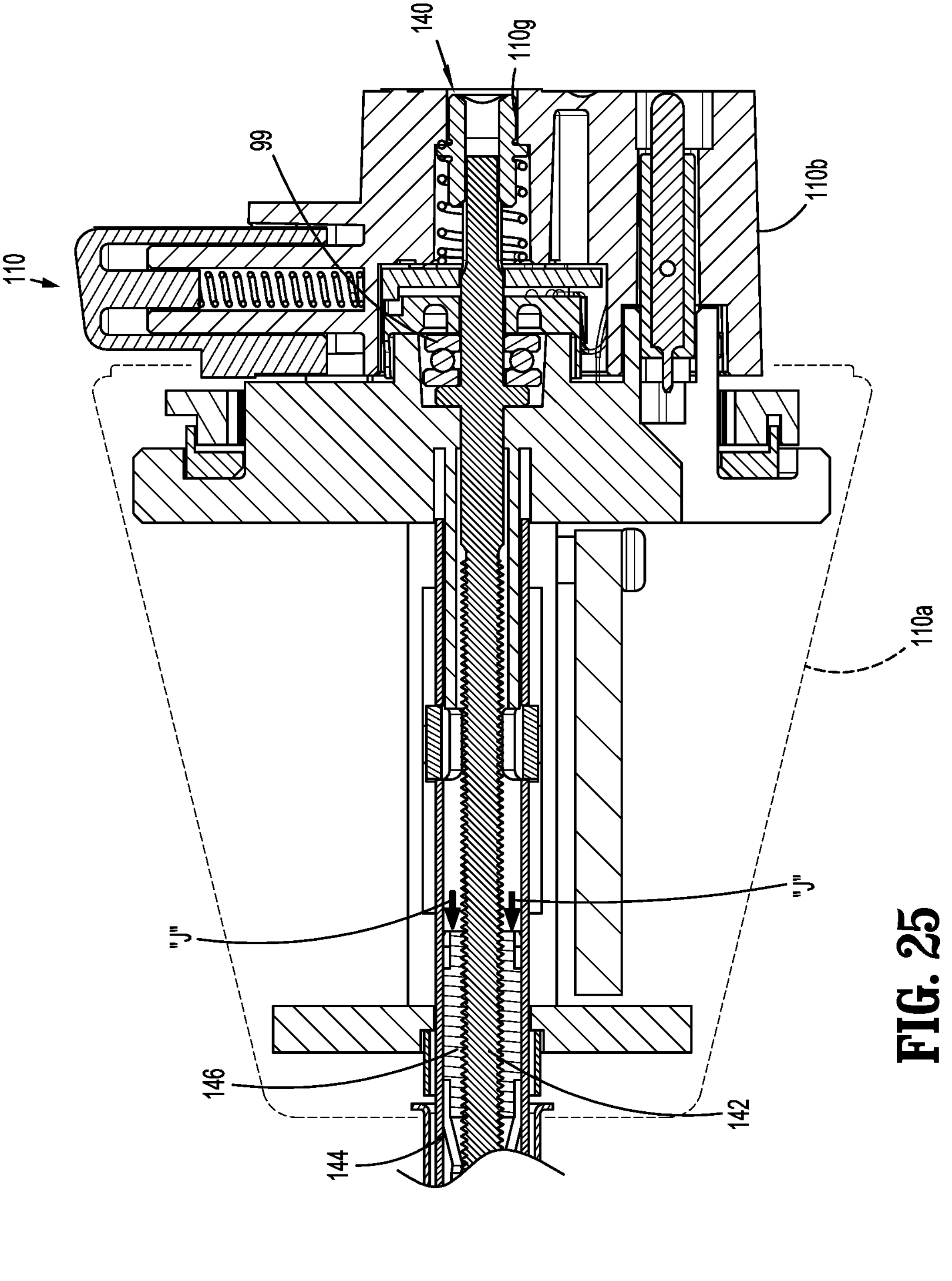
FIG. 25 is a cross-sectional view of a proximal portion of the elongated shaft assembly with portions thereof shown in phantom for clarity.
Figures 26, 27:
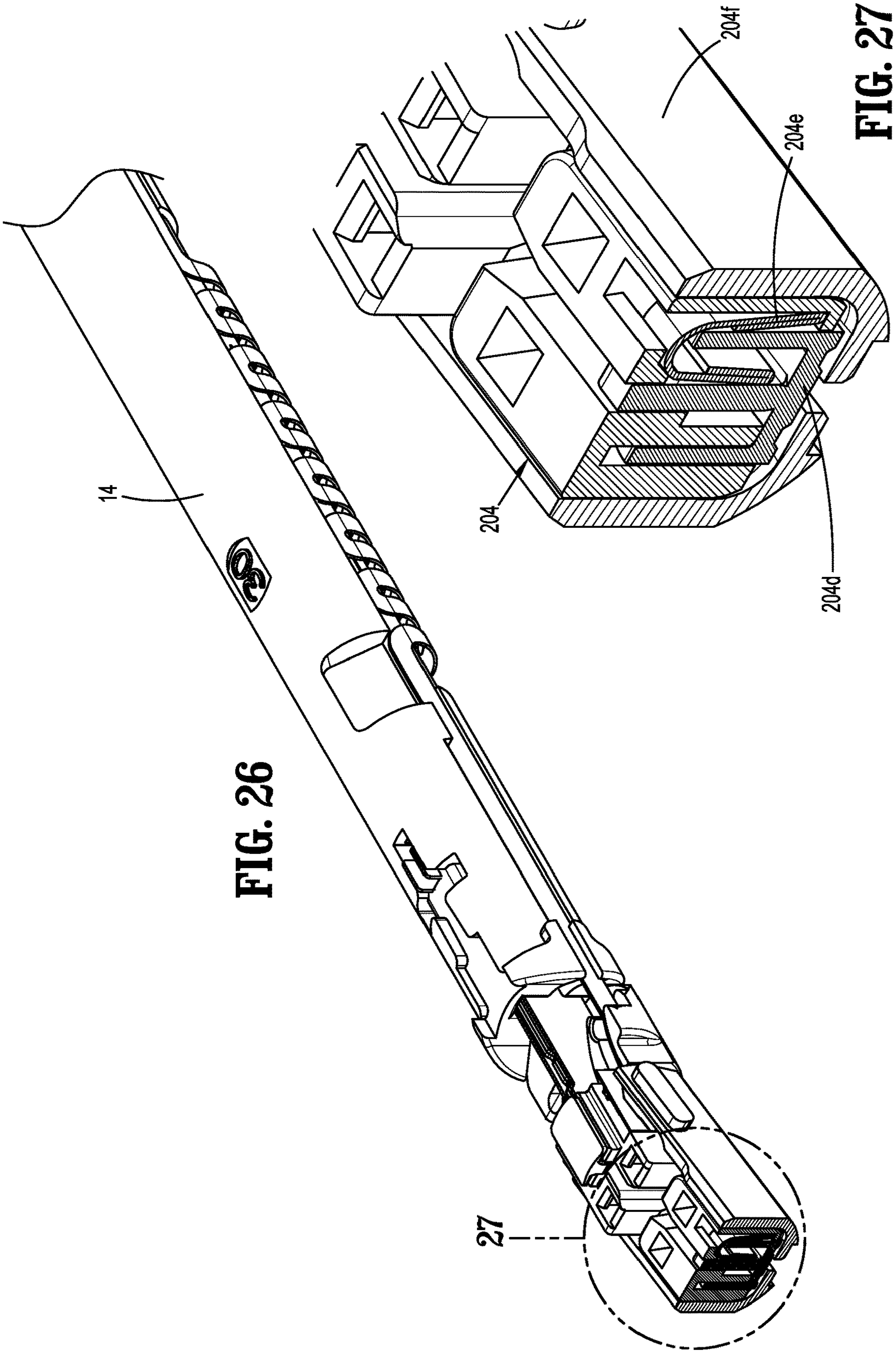
FIG. 26 is a perspective, cross-sectional view of the elongated shaft assembly as taken along section line 26-26 shown in FIG. 10.
FIG. 27 is an enlarged view of the indicated area of detail shown in FIG. 26.
Figure 28:
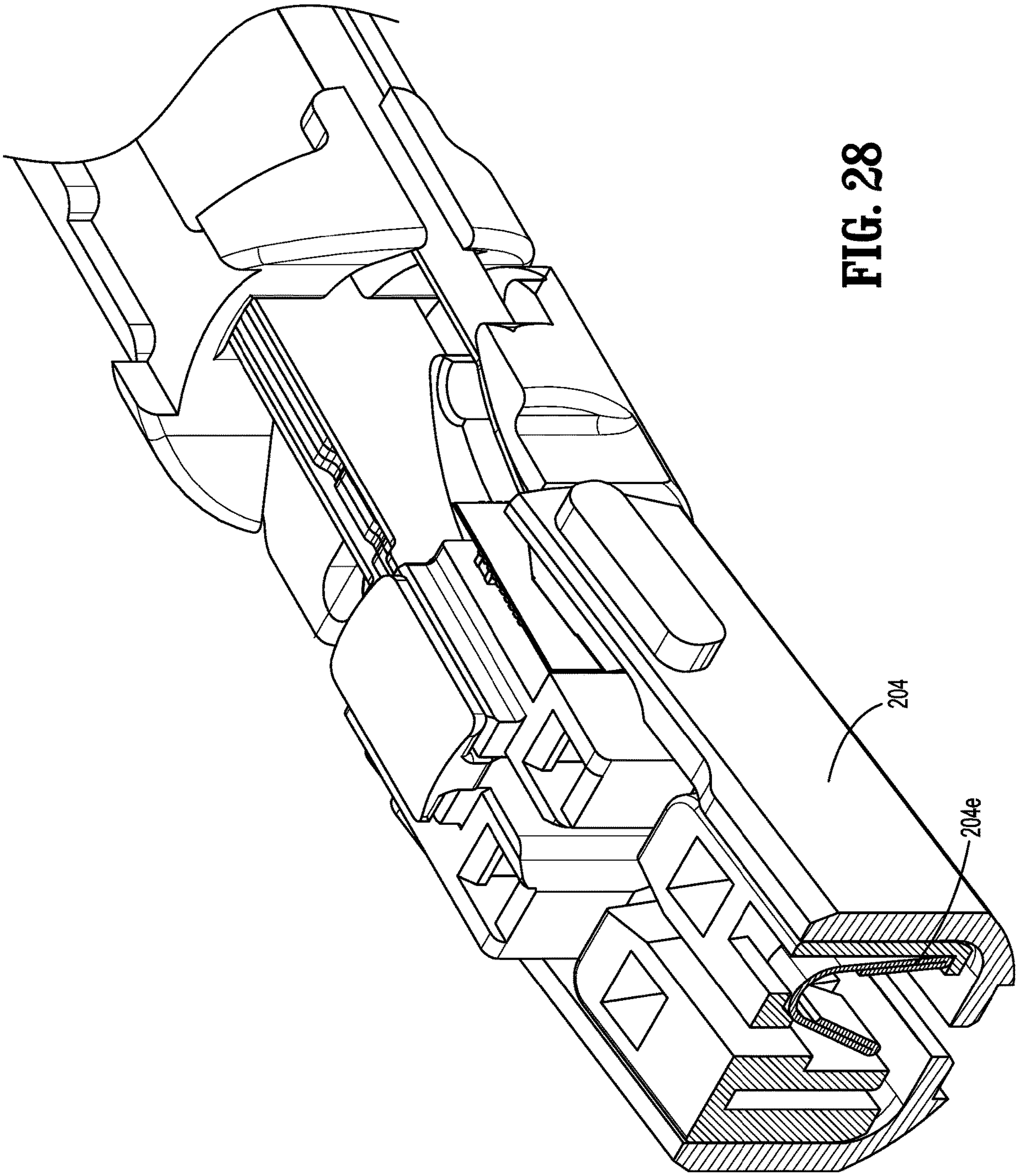
FIG. 28 is an enlarged view of a distal portion of FIG. 26 illustrating the lockout spring of FIG. 7 in a locked position.

Firing assembly 140 of adapter assembly 100 includes second actuator 110*y* on a proximal end portion thereof that mechanically engages with drive mechanism 12*h* of housing assembly 12. Firing assembly 140 further includes a firing drive screw 142 that is mechanically coupled to second actuator 110*y* and extends distally therefrom and through inner body assembly 111. Firing drive screw 142 is rotatably supported within inner housing assembly 111 by a bearing assembly 99. A distal portion of firing drive screw 142 is coupled to a proximal end portion of a firing tube 144 via a firing nut 146 threadedly mounted on firing drive screw 142 to enable firing nut 146 to translate in response to rotation of firing drive screw 142. Firing nut 146 includes elongated ribs 146*a* disposed in spaced-apart relation to one another about an outer surface of firing nut 146. Firing nut 146 further includes an elongated lug 146*b* that extends along an outer surface of firing nut 146 and radially farther outward from the outer surface of firing nut 146 than elongated ribs 146*a* to enable firing nut 146 to translate along articulation tube 128 as elongated lug 146*b* of firing nut 146 slides through a slide channel 128*b* (FIG. 9) defined through articulation tube 128. In this regard, elongated lug 146*b* functions as a keel to prevent rotations as firing nut 146 rides along slide channel 128*b* of articulation tube 128. Firing tube 144 includes a split collar 144*a* on a proximal end portion thereof that interlocks with elongated ribs 146*a* of firing nut 146 to prevent rotation of firing nut 146 about longitudinal axis "L" when firing drive screw 142 is rotated to distally advance firing tube 144, as indicated by arrows "J" (FIG. 25). This interlocking structure of the split collar 144*a* and elongated ribs 146*a* of firing nut 146 functions as a collet and provides a low-profile design that enables firing drive screw 142 to have an increased diameter such as would be suitable for a 12 mm passage design (as opposed to the smaller diameter 8 mm passage design for which surgical stapling apparatus 10 may be utilized). A distal portion of firing tube 144 is secured to a proximal end portion of a firing rod 148 by an interlocking joint 149. The interlocking joint 149 functions to reduce overall diameter and includes a female member 144*b* on a distal end portion of firing tube 144 and a male member 148*a* on proximal end portion of firing rod 148. A distal end portion of firing rod 148 is mechanically coupled to a proximal end portion of drive beam assembly 150 via a transverse rod 148*b* (FIG. 18) supported on distal end portion of firing rod 148.

Drive beam assembly 150 of firing assembly 140 includes a plurality of laminates 150*a*, 150*b*, 150*c* having proximal hooks 151 that are secured to a distal end portion of firing rod 148. The laminates 150*a*, 150*b*, 150*c* have distal end portions that are secured to a drive beam 152 including a knife 152*a* thereon. Drive beam 152 is selectively distally advanceable through end effector 200 to drive sled 204*d* therethrough when firing rod 148 advances laminates 150*a*, 150*b*, 150*c*. When drive beam 152 distally advances, anvil and cartridge assemblies 202, 204 are configured to move from an open position to a closed position to clamp on tissue therebetween. Further distal advancement of drive beam 152 causes knife 152*a* of drive beam 152 to cut the clamped tissue as drive beam 152 engages and distally advances drive sled 204*d* through cartridge assembly 204 for causing fasteners supported therein be formed against anvil assembly 202 and secured to the clamped tissue between anvil and cartridge assemblies 202, 204. Once fired, drive beam assembly 150 can be retracted proximally away from sled 204*d* and proximal to spring lock 204*e* of cartridge assembly 204 such that spring lock 204*e*, which is disposed in an open or locked position (FIG. 28) after sled 204*d* is distally advanced, prevents further distal advancement of drive beam assembly 150 after drive beam assembly 150 is retracted to an initial position thereof.

Rotation assembly 160 of adapter assembly 100 includes third actuator 110*x* on a proximal end portion thereof that mechanically engages with drive mechanism 12*h* of housing assembly 12. Rotation assembly 160 further includes a driver 162 that is mechanically coupled to third actuator 110*x* and extends distally therefrom through actuator mount 113 and into inner body assembly 111. Driver 162 has a non-circular distal drive 162*a* to facilitate non-rotational coupling to a pinion 164 so that pinion 164 rotates with driver 162 as third actuator 110*x* is rotated. Pinion 164 (e.g., teeth on an outer surface thereof) is enmeshed with an annulus 166 (e.g., teeth on an inner surface thereof) having opposed mounting tabs 166*a* extending from diametrically opposed ends of an outer surface of annulus 166. Opposed mounting tabs 166*a* are mounted within tab recesses 110*g* defined within distal outer housing 110*b*. Tabs 166*a* of annulus 166 secure annulus 166 to upper housing 110*e* and to lower housing 110*f* of distal outer housing 110*b* so that distal outer housing 110*b* rotates relative to proximal outer housing 110*a* as annulus 166 is rotated by pinion 164. Rotation of distal housing 110*b* causes outer tube 109 and end effector 200 to rotate about longitudinal axis "L." Rotation assembly 160 further includes a rotation ring 168 that receives annulus 166 and is supported by a proximal end portion of inner body assembly 111. Rotation ring 168 includes a stop tab 168*a* on an outer surface thereof that is positioned to engage a stop tab 111*a* depending from inner body assembly 111, whereby stop tabs 168*a*, 111*a* are positioned to function as a slip stop that enables rotation assembly 160 to rotate up to about 700 degrees. Rotation ring 168 is configured to rotate at half speed (e.g., float) such that rotation ring 168 enables two full rotations (e.g., up to about 700 degrees) minus a thickness of stop tab 168*a* thereof.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical workstations and/or components thereof, reference may be made to U.S. Patent Application Publication No. 2012/0116416, and PCT Application Publication No. WO2016/025132, the entire contents of each of which are incorporated by reference herein.

Moreover, the disclosed electronic structure such as the controller(s), can include any suitable electrical components for operating the disclosed surgical stapling apparatus or components thereof. Such electrical components can include, for example, one or more controllers and/or circuitry, which may include or be coupled to one or more printed circuit boards. As used herein, the term "controller" includes "processor," "digital processing device" and like terms, and are used to indicate a microprocessor or central processing unit (CPU). The CPU is the electronic circuitry within a computer that carries out the instructions of a computer program by performing the basic arithmetic, logical, control and input/output (I/O) operations specified by the instructions, and by way of non-limiting examples, include server computers. In some aspects, the controller includes an operating system configured to perform executable instructions. The operating system is, for example, software, including programs and data, which manages hardware of the disclosed surgical stapling apparatus and provides services for execution of applications for use with the disclosed surgical stapling apparatus. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. In some aspects, the operating system is provided by cloud computing.

In some aspects, the term "controller" may be used to indicate a device that controls the transfer of data from a computer or computing device to a peripheral or separate device and vice versa, and/or a mechanical and/or electromechanical device (e.g., a lever, knob, etc.) that mechanically operates and/or actuates a peripheral or separate device.

In aspects, the controller includes a storage and/or memory device. The storage and/or memory device is one or more physical apparatus used to store data or programs on a temporary or permanent basis. In some aspects, the controller includes volatile memory and requires power to maintain stored information. In various aspects, the controller includes non-volatile memory and retains stored information when it is not powered. In some aspects, the non-volatile memory includes flash memory. In certain aspects, the non-volatile memory includes dynamic random-access memory (DRAM). In some aspects, the non-volatile memory includes ferroelectric random-access memory (FRAM). In various aspects, the non-volatile memory includes phase-change random access memory (PRAM). In certain aspects, the controller is a storage device including, by way of non-limiting examples, CD-ROMs, DVDs, flash memory devices, magnetic disk drives, magnetic tapes drives, optical disk drives, and cloud-computing based storage. In various aspects, the storage and/or memory device is a combination of devices such as those disclosed herein.

In some aspects, the controller includes a display to send visual information to a user. In various aspects, the display is a cathode ray tube (CRT). In various aspects, the display is a liquid crystal display (LCD). In certain aspects, the display is a thin film transistor liquid crystal display (TFT-LCD). In aspects, the display is an organic light emitting diode (OLED) display. In certain aspects, on OLED display is a passive-matrix OLED (PMOLED) or active-matrix OLED (AMOLED) display. In aspects, the display is a plasma display. In certain aspects, the display is a video projector. In various aspects, the display is interactive (e.g., having a touch screen or a sensor such as a camera, a 3D sensor, a LiDAR, a radar, etc.) that can detect user interactions/gestures/responses and the like. In some aspects, the display is a combination of devices such as those disclosed herein.

The controller may include or be coupled to a server and/or a network. As used herein, the term “server” includes “computer server,” “central server,” “main server,” and like terms to indicate a computer or device on a network that manages the surgical stapling apparatus, components thereof, and/or resources thereof. As used herein, the term “network” can include any network technology including, for instance, a cellular data network, a wired network, a fiber optic network, a satellite network, and/or an IEEE 802.11a/b/g/n/ac wireless network, among others.

In various aspects, the controller can be coupled to a mesh network. As used herein, a “mesh network” is a network topology in which each node relays data for the network. All mesh nodes cooperate in the distribution of data in the network. It can be applied to both wired and wireless networks. Wireless mesh networks can be considered a type of “Wireless ad hoc” network. Thus, wireless mesh networks are closely related to Mobile ad hoc networks (MANETs). Although MANETs are not restricted to a specific mesh network topology, Wireless ad hoc networks or MANETs can take any form of network topology. Mesh networks can relay messages using either a flooding technique or a routing technique. With routing, the message is propagated along a path by hopping from node to node until it reaches its destination. To ensure that all its paths are available, the network must allow for continuous connections and must reconfigure itself around broken paths, using self-healing algorithms such as Shortest Path Bridging. Self-healing allows a routing-based network to operate when a node breaks down or when a connection becomes unreliable. As a result, the network is typically quite reliable, as there is often more than one path between a source and a destination in the network. This concept can also apply to wired networks and to software interaction. A mesh network whose nodes are all connected to each other is a fully connected network.

In some aspects, the controller may include one or more modules. As used herein, the term “module” and like terms are used to indicate a self-contained hardware component of the central server, which in turn includes software modules. In software, a module is a part of a program. Programs are composed of one or more independently developed modules that are not combined until the program is linked. A single module can contain one or several routines, or sections of programs that perform a particular task.

As used herein, the controller includes software modules for managing various aspects and functions of the disclosed surgical stapling apparatus or components thereof.

The disclosed surgical stapling apparatus may also utilize one or more controllers to receive various information and transform the received information to generate an output. The controller may include any type of computing device, computational circuit, or any type of processor or processing circuit capable of executing a series of instructions that are stored in memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

Any of the herein described methods, programs, algorithms, or codes may be converted to, or expressed in, a programming language or computer program. The terms “programming language” and “computer program,” as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

As can be appreciated, securement of any of the components of the disclosed apparatus can be effectuated using known securement techniques such welding, crimping, gluing, fastening, etc. Also, any of the disclosed structure can include any suitable conductive material (e.g., metallic), semi-conductive material (e.g., silicone), and/or non-conductive/insulative material (e.g., plastic).

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical stapling apparatus, comprising:
a housing assembly; and
an adapter assembly defining a longitudinal axis and selectively attachable to the housing assembly, the adapter assembly supporting an end effector, the end effector including:
an anvil assembly;
a cartridge assembly supporting a plurality of fasteners and a sled that is movable through the cartridge assembly to fire the plurality of fasteners; and
a spring lock supported on an inner surface of the sled when the spring lock is in an unlocked position, the spring lock positioned to move from the unlocked position to a locked and open position when the sled moves distally and away from the spring lock through the cartridge assembly to prevent the cartridge assembly from being refired.

2. The surgical stapling apparatus of claim 1, further comprising a firing assembly supported in the adapter assembly, the firing assembly including a firing drive screw threadedly coupled to a firing nut.

3. The surgical stapling apparatus of claim 2, wherein the firing nut translates in response to rotation of the firing drive screw.

4. The surgical stapling apparatus of claim 3, wherein the firing nut includes elongated ribs that interlock with a split collar of a firing tube to prevent rotation of the firing nut.

5. The surgical stapling apparatus of claim 4, wherein a firing rod is secured to a distal end portion of the firing tube.

6. The surgical stapling apparatus of claim 5, wherein the firing rod is coupled to a drive beam assembly that is advanceable through the end effector.

7. The surgical stapling apparatus of claim 6, wherein the firing rod is positioned to advance the drive beam assembly through the end effector when the firing tube translates the firing rod distally.

8. The surgical stapling apparatus of claim 1, further comprising a rotation assembly having a driver coupled to a pinion, and wherein rotation of the driver causes the end effector to rotate about the longitudinal axis.

9. The surgical stapling apparatus of claim 8, wherein the pinion is coupled to an annulus and the annulus is coupled to a housing on a proximal end portion of the adapter assembly.

10. The surgical stapling apparatus of claim 9, wherein the housing is coupled to an outer tube and the outer tube is coupled to the end effector.

11. A surgical stapling apparatus, comprising:
a housing assembly;
an elongated shaft assembly defining a longitudinal axis and having a distal end portion and a proximal end portion, the proximal end portion selectively attached to the housing assembly;
an anvil assembly supported on the distal end portion of the elongated shaft assembly;
a cartridge assembly selectively attached to the anvil assembly to secure the cartridge assembly to the elongated shaft assembly, the cartridge assembly supporting a plurality of fasteners and a sled that is movable through the cartridge assembly to fire the plurality of fasteners; and
a spring lock supported on an inner surface of the sled when the spring lock is in an unlocked position, the spring lock positioned to move from the unlocked position to a locked and open position when the sled moves distally and away from the spring lock through the cartridge assembly to prevent the cartridge assembly from being refired.

12. The surgical stapling apparatus of claim 11, further comprising a firing drive screw coupled to a firing nut.

13. The surgical stapling apparatus of claim 12, wherein the firing nut translates in response to rotation of the firing drive screw.

14. The surgical stapling apparatus of claim 12, further comprising an articulation tube that is moveable to cause the anvil and cartridge assemblies to articulate relative to the longitudinal axis.

15. The surgical stapling apparatus of claim 14, wherein the firing drive screw is disposed within the articulation tube.

16. The surgical stapling apparatus of claim 11, wherein the anvil assembly includes anvil tissue stops defining cartridge tab slots therethrough, and wherein the cartridge assembly includes proximal tabs that are receivable within the cartridge tab slots of the anvil assembly to couple the cartridge assembly to the anvil assembly.

17. An adapter assembly of a surgical stapling apparatus, the adapter assembly comprising:
a proximal housing;
an elongated shaft assembly coupled to the proximal housing and defining a longitudinal axis, the elongated shaft assembly having a proximal end portion and a distal end portion; and
an end effector supported on the distal end portion of the elongated shaft assembly, the end effector including:
an anvil assembly;
a cartridge assembly selectively attached to the anvil assembly, the cartridge assembly supporting a plurality of fasteners and a sled that is movable through the cartridge assembly to fire the plurality of fasteners; and
a spring lock supported on an inner surface of the sled when the spring lock is in an unlocked position, the spring lock positioned to move from the unlocked position to a locked and open position when the sled moves distally and away from the spring lock through the cartridge assembly to prevent the cartridge assembly from being refired.

18. The adapter assembly of claim 17, further comprising a firing assembly including a firing drive screw threadedly coupled to a firing nut, the firing nut coupled to a firing tube wherein the firing tube is axially advanceable in response to axial movement of the firing nut.

19. The adapter assembly of claim 18, wherein a firing rod is secured to the firing tube, the firing rod coupled to a drive beam assembly and positioned to advance the drive beam assembly through the end effector when the firing tube translates the firing rod distally.

20. The adapter assembly of claim 17, further comprising a rotation assembly having a driver coupled to a pinion, and wherein rotation of the driver causes the end effector to rotate about the longitudinal axis.

* * * * *